US012594421B2

(12) United States Patent
Voloshin-Sela et al.

(10) Patent No.: US 12,594,421 B2
(45) Date of Patent: Apr. 7, 2026

(54) COMPOSITIONS AND METHODS FOR INCREASING CANCER CELL SENSITIVITY TO ALTERNATING ELECTRIC FIELDS

(71) Applicant: NOVOCURE GMBH, Root (CH)

(72) Inventors: Tali Voloshin-Sela, Haifa (IL); Lilach Avigdor, Haifa (IL); Anat Klein-Goldberg, Haifa (IL)

(73) Assignee: NOVOCURE GMBH, Baar (CH)

( * ) Notice: Subject to any disclaimer, the term of this patent is extended or adjusted under 35 U.S.C. 154(b) by 743 days.

(21) Appl. No.: 17/393,097

(22) Filed: Aug. 3, 2021

(65) Prior Publication Data

US 2022/0096818 A1 Mar. 31, 2022

Related U.S. Application Data

(60) Provisional application No. 63/119,332, filed on Nov. 30, 2020, provisional application No. 63/060,506, filed on Aug. 3, 2020.

(51) Int. Cl.
*A61N 1/36* (2006.01)
*A61K 31/426* (2006.01)
(Continued)

(52) U.S. Cl.
CPC ........ *A61N 1/36002* (2017.08); *A61K 31/426* (2013.01); *A61K 31/519* (2013.01); *A61K 31/5377* (2013.01); *A61K 45/06* (2013.01)

(58) Field of Classification Search
CPC .............................................. A61N 11/36002
(Continued)

(56) References Cited

U.S. PATENT DOCUMENTS

2012/0310140 A1* 12/2012 Kramer ................ A61K 9/0085
604/93.01
2018/0154142 A1* 6/2018 Guo .................... A61B 18/1206
2019/0307781 A1* 10/2019 Krex ...................... A61K 45/06

FOREIGN PATENT DOCUMENTS

WO WO 2018/106672 A1 6/2018

OTHER PUBLICATIONS

Tian L, Wang L, Qiao Y, Lu L, Lee P, Chang A, Ravi S, Rogers TA, Melancon MP. Antitumor Efficacy of Liposome-Encapsulated NVP-BEZ235 Combined with Irreversible Electroporation for Head and Neck Cancer. Molecules. Oct. 1, 2019;24(19):3560. (Year: 2019).*
(Continued)

*Primary Examiner* — Jennifer Pitrak McDonald
*Assistant Examiner* — Christine Sison
(74) *Attorney, Agent, or Firm* — Ballard Spahr LLP

(57) ABSTRACT

Disclosed herein are methods for increasing sensitivity of a cancer cell to alternating electric fields by administering an AKT inhibitor, a mammalian target of rapamycin (mTOR) inhibitor, a Phosphatidylinositol 3-Kinase (PI3K) inhibitor, and/or a Glycogen synthase kinase 3β (GSK3β) inhibitor. Disclosed are methods of increasing treatment efficacy comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, or GSK3β inhibitor to the subject. Disclosed are methods of reducing viability of cancer cells using alternating electric fields for a period of time, the alternating electric fields having a frequency and field strength in combination with either an mTOR inhibitor, AKT inhibitor, PI3K inhibitor, or GSK3β inhibitor and/or a composition or compound that increases cyclin D1. Disclosed are methods of increasing apoptosis of a cancer cell
(Continued)

comprising exposing the cancer cell to alternating electric fields for a period of time, the alternating electric fields having a frequency and field strength; and exposing the cancer cell to a PI3K inhibitor.

18 Claims, 20 Drawing Sheets

(51) Int. Cl.
  *A61K 31/519* (2006.01)
  *A61K 31/5377* (2006.01)
  *A61K 45/06* (2006.01)
(58) Field of Classification Search
  USPC .......................................................... 607/3
  See application file for complete search history.

(56) References Cited

OTHER PUBLICATIONS

Kirson ED, Gurvich Z, Schneiderman R, Dekel E, Itzhaki A, Wasserman Y, Schatzberger R, Palti Y. Disruption of cancer cell replication by alternating electric fields. Cancer Res. May 1, 2004;64(9):3288-95. (Year: 2004).*
Koul D, Shen R, Kim YW, Kondo Y, Lu Y, Bankson J, Ronen SM, Kirkpatrick DL, Powis G, Yung WK. Cellular and in vivo activity of a novel PI3K inhibitor, PX-866, against human glioblastoma. Neuro Oncol. Jun. 2010;12(6):559-69. (Year: 2010).*
Hernández-Bule ML, Cid MA, Trillo MA, Leal J, Ubeda A. Cytostatic response of HepG2 to 0.57 MHz electric currents mediated by changes in cell cycle control proteins. Int J Oncol. Dec. 2010;37(6):1399-405. (Year: 2010).*
Sheikh AQ, Taghian T, Hemingway B, Cho H, Kogan AB, Narmoneva DA. Regulation of endothelial MAPK/ERK signalling and capillary morphogenesis by low-amplitude electric field. J R Soc Interface. Jan. 6, 2013;10(78):20120548. doi: 10.1098/rsif.2012.0548. Epub Sep. 19, 2012. PMID: 22993248; PMCID: PMC3565781. (Year: 2013).*
U.S. Appl. No. 63/119,332, filed Nov. 30, 2020, Voloshin-Tela (Novocure).
U.S. Appl. No. 63/060,506, filed Sep. 25, 2020, Voloshin-Tela (Novocure).
PCT, PCT/IB2021057107 (WO 2022/029628, Sep. 17, 2021 (Feb. 10, 2022, Voloshin-Tela (Novocure).
Atabay, K.D. and Karabay, A. "Pin 1 inhibition activates cyclin D and produces neurodegenerative pathology." Journal of neurochemistry (2012) 120:430-439.
Bonnet et al. "Dehydroepiandrosterone Reverses Systemic Vascular Remodeling Through the Inhibition of the Akt/GSK3-βNFAT Axis." Circulation 120: 1231-1240 (2009).
Buttrick et al. "PI3-K and GSK-3: Akt-ing Together with Microtubules." Cell Cycle 7:17, 2621-2625 (2008).
Chen et al. "Celecoxib Promotes c-FLIP Degradation Through Akt-Independent Inhibition of GSK3." Cancer Research 71(19): 6270-6281 (2011).
Dai et al. "Nanosecond Pulsed electric fileds enhance the anti-tumour effects of the mTOR inhibitor Everolimus against melanoma." Scientific reports. 7:39597, Jan. 2017.
Desbois-Mouthon et al. "Insulin and IGF-1 Stimulate the β-catenin Pathway Through Two Signaling Cascades Involving GSK-3β Inhibition and Ras Activation." (2001).
Engel et al. "The Retinoblastoma Protein: A Mater Tumor Suppressor Acts as a Link Between Cell Cycle and Cell Adhesion." Cell Health Cytoskelet 7: 1-10 (2015).
Germain et al. "Ubiquitination of Free Cyclin D1 is Independent of Phosphorylation on Threonine 286." The Journal of Biological Chemistry, 275(16): 12074-12079 (2000).

Kim et al. "Overexpression of cell cycle proteins of peripheral lymphocytes in patients with Alzheimer's disease." Psychiatry Investig 2016;13(1):127-134.
Li et al. "Cyclin D1 regulates cellular migration through the inhibition of thrombospondin1 and ROCK signaling". Molecular and cellular biology (2006) 26: 4240-4256.
Masamha et al. "Cyclin D1 Degradation is Sufficient to Induce G1 Cell Cycle Arrest Despite Constitutive Expression of Cyclin E2 in Ovarian Cancer Cells". Cancer Res. 69(16):6565-6572 (2009).
Nakayama et al. "Helicobacter pylori VacA-induced Inhibition of GSK3 Through the PI3K/Akt Signaling Pathway." Journal of Biological Chemistry 284(3):1612-1619 (2009).
Neumeister et al. "Cyclin D1 governs adhesion and motility of macrophages" Molecular biology of the cell (2003) 14: 2005-2015.
Noorolyai et al. "The relation between PI3K/AKT signalling pathway and cancer", Gen (2019) 698: 120-128, 2019.
Rommel et al. "Mediation of IGF-1-Induced Skeletal Myotube Hypertrophy by PI(3)K/Akt/mTOR and PI(3)K/Akt/GSK3 Pathways." Nature Cell Biology, vol. 3, pp. 1009-1013 (2001).
Seo, J. and Park, M. "Molecular crosstalk between cancer and neurodegenerative diseases." Cellular and Molecular Life Sciences (2020) 77:2659-2680.
Tsang et al. "Cyclin D1 overexpression supports stable EBV infection in nasopharyngeal epithelial cells," PNAS (2012) E3473-E3482 PNAS.
Tseng et al. "The GSK-3 Inhibitor BIO Promotes Proliferation in Mammalian Cardiomyocytes." Chemistry & Biology 13: 957-963 (2006).
Tyagi et al. "Inhibition of Retinoblastoma Protein (Rb) Phosphorylation at Serine Sites and an Increase in RB-EsF Complex Formation by Silibinin in Androgen-Dependent Human Prostate Carcinoma LNCaP Cells: Role in Prostate Cancer Prevention." Molecular Cancer Therapeutics vol. 1: 525-532 (2002).
Wen et al. "Buparlisib in Patients With Recurrent Glioblastoma Harboring Phosphatidylinositol 3-Kinase Pathway Activation: An Open-Label, Multicenter, Multi-Arm, Phase II Trial", Journal of Clinical Oncology (2019) 37:9:741-750.
Whittaker et al. "The Cyclin-Dependent Kinase Inhibitor CYC202 (R-Roscovitine) Inhibits Retinoblastoma Protein Phosphorylation, Causes Loss of Cyclin D1, and Activates the Mitogen-Activated Protein Kinase Pathway." Cancer Research 64:262-272 (2004).
Yang et al. "Myostatin Induces Cyclin D1 Degradation to Cause Cell Cycle Arrest Through a Phosphatidylinositol 3-Kinase/AKT/GSK-3β Pathway and Is Antagonized by Insulin-like Growth Factor 1." The Journal of Biologoical Chemistry, vol. 282(6): 3799-3808 (2007).
Yang et al. "Targeting PI3K in cancer: mechanisms and advances in clinical trials." Molecular Cancer (2019) 18:26.
Yu et al. "Proliferation, Survival and Metabolism: the Role of PI3K/AKT/mTOR signaling in Pluripotency and Cell Fate Determination." Review Development 143: 3050-3060 (2016).
Zhang et al. "S6K1 Regulates GSK3 Under Conditions of mTOR-Dependent Feedback Inhibition of Akt." Molecular Cell 24:185-197 (2006).
International Preliminary Report on Patentability mailed Feb. 7, 2023 by the IB for International Application PCT/IB2021/057107, filed Aug. 3, 2021 (14 pages).
Written Opinion and International Search Report mailed Jan. 4, 2022 by the EPO for International Application PCT/IB2021/057107, filed Aug. 3, 2021 (18 pages).
Tian Li et al. Antittumor Efficacy of Liposome-encapsulated NVP-BEZ235 Combined with Irreversible Electroporation for Head and Neck Cancer, Molecules 24, 3560 (2019).
Klein-Goldberg Anat et al. "Abstract 1382: Targeting Akt signaling pathway potentiates the antitumor effect of Tumor Treating Fields (TTFields) in vitro", Cancer Research, Jul. 31, 2021.
Ansstas, G., et al., "Treatment with Tumor-Treating Fields Therapy and Pulse Dose Bevacizumab in Patients with Bevacizumab-Refractory Recurrent Glioblastoma: A Case Series," Case Reports in Neurology Switzerland, 8(1): 1-9 (2015).
Garg, A., et al., "Non-Contact Electric Fields Potently Hinder EGF Promoted Breast Cancer Motility by Downregulating EGFR Phosphorlation," The FASEB Journal, 32(S1), (2018).

(56) References Cited

OTHER PUBLICATIONS

Garg, A., et al., "Electromagnetic fields alter the motility of metastatic breast cancer cells," Communications Biology, 2(1), (2019).
Lee, B., et al., "FAK signaling in human cancer as a target for therapeutics," Pharmacology & Therapeutics, 146: 132-149 (2014).
Rick, J., et al., "Tumor treating fields a new approach to glioblastoma therapy," Journal of Neuro-oncology, 137(3): 447-453 (2018).
Yan, X.L., et al., "Observation of the effects of physiological range direct-current electric fields effect on apoptosis and cell cycle of lung cancer cells," Chinese Journal of Cancer Prevention and Treatment, pp. 985-988, and 996 (2011).

* cited by examiner

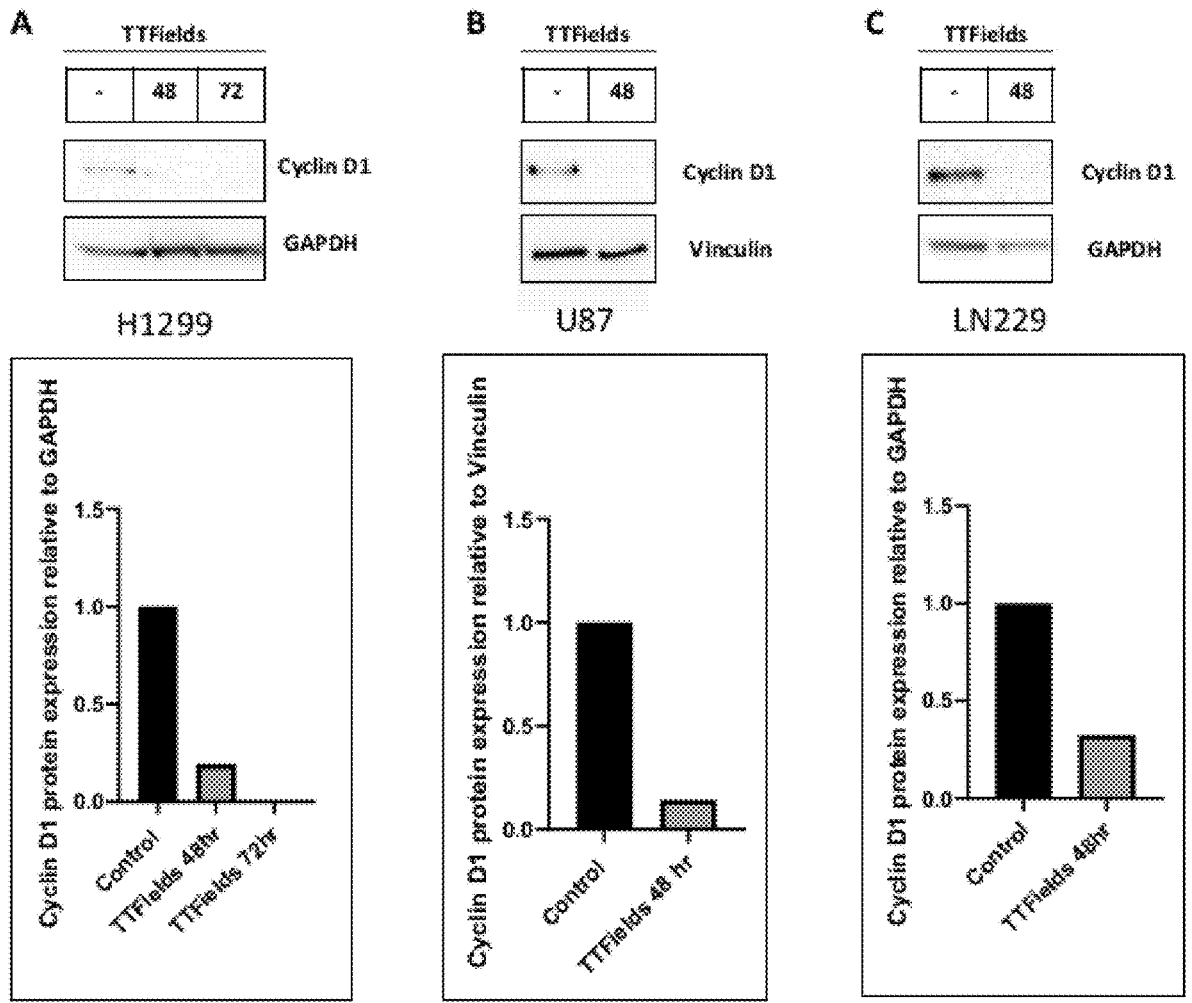
FIG. 2A, FIG. 2B, FIG. 2C,

Inhibitor = Dasatinib

IC25 = inhibition concentration of 25%

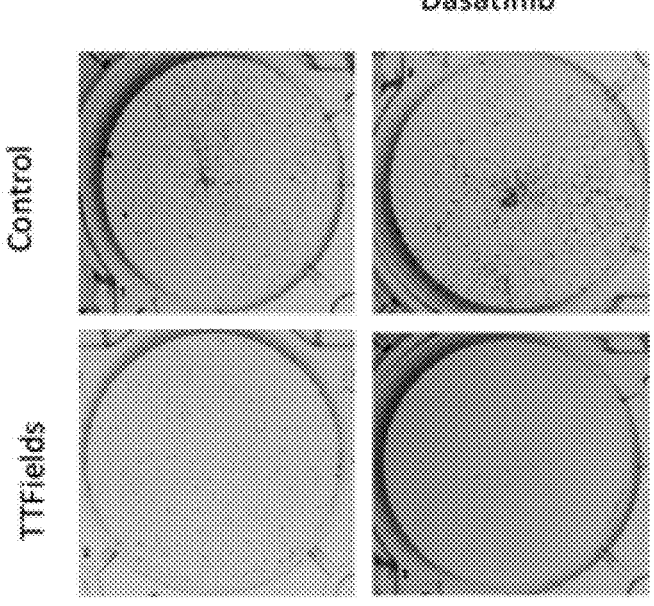
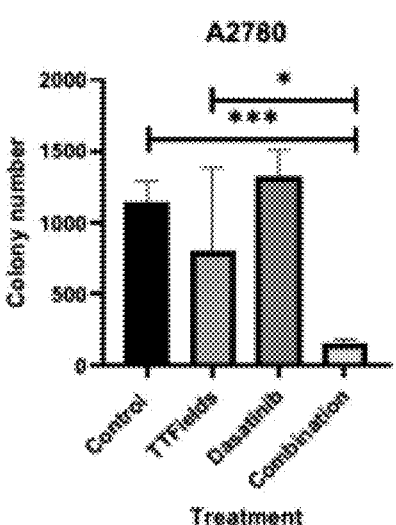
FIG. 15

COMPOSITIONS AND METHODS FOR INCREASING CANCER CELL SENSITIVITY TO ALTERNATING ELECTRIC FIELDS

CROSS-REFERENCE TO RELATED APPLICATIONS

This application claims the benefit of U.S. Provisional Patent Application No. 63/060,506, filed on Aug. 3, 2020 and U.S. Provisional Patent Application No. 63/119,332, filed on Nov. 30, 2020, each of which is incorporated by reference herein in its entirety.

BACKGROUND

Tumor Treating Fields, or TTFields, are low intensity (e.g., 1-3 V/cm) alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. TTFields are FDA approved for the treatment of glioblastoma (GBM), and may be delivered, for example, via the Optune™ system. Optune™ includes a field generator and two pairs of transducer arrays (i.e., electrode arrays) that are placed on a patient's shaved head. One pair of electrodes is positioned to the left and right of the tumor, and the other pair of electrodes is positioned anterior and posterior to the tumor. In the preclinical setting, TTFields can be applied in vitro using, for example, the Inovitro™ TTFields lab bench system.

TTFields therapy is an approved mono-treatment for recurrent glioblastoma, and an approved combination therapy with chemotherapy for newly diagnosed glioblastoma and unresectable malignant pleural mesothelioma patients. These electric fields are induced non-invasively by transducer arrays (i.e., arrays of electrodes) placed directly on the patient's scalp. TTFields also appear to be beneficial for treating tumors in other parts of the body.

Disclosed herein are combination therapies using alternating electric fields (e.g. a TTFields) and one or more of an mTOR inhibitor, AKT inhibitor, PI3K inhibitor, Src inhibitor, Fak inhibitor, or GSK3β inhibitor to help increase a cancer cells sensitivity to the alternating electric fields.

BRIEF SUMMARY

Disclosed herein are methods for increasing sensitivity of a cancer cell to alternating electric fields by administering an AKT inhibitor, a mammalian target of rapamycin (mTOR) inhibitor, a Phosphatidylinositol 3-Kinase (PI3K) inhibitor, Src tyrosine kinase (Src) inhibitor, Focal adhesion kinase (Fak) inhibitor, and/or a Glycogen synthase kinase 3β (GSK3β) inhibitor.

Disclosed are methods of increasing sensitivity of a cancer cell to alternating electric fields comprising exposing the cancer cell to alternating electric fields for a period of time, the alternating electric fields having a frequency and field strength, wherein the frequency and field strength of the alternating electric fields, and exposing the cancer cell to an mTOR inhibitor, AKT inhibitor, PI3K inhibitor, Src inhibitor, Fak inhibitor, and/or GSK3β inhibitor.

Disclosed are methods of increasing treatment efficacy comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor to the subject.

Disclosed are methods of treating a subject having cancer comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor to the subject.

Disclosed are methods of reducing viability of cancer cells using alternating electric fields for a period of time, the alternating electric fields having a frequency and field strength in combination with either an mTOR inhibitor, AKT inhibitor, PI3K inhibitor, Src inhibitor, Fak inhibitor, or GSK3β inhibitor and/or a composition or compound that increases cyclin D1.

Disclosed are methods of increasing apoptosis of a cancer cell comprising exposing the cancer cell to alternating electric fields for a period of time, the alternating electric fields having a frequency and field strength; and exposing the cancer cell to a PI3K inhibitor.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2A, FIG. 2B, and FIG. 2C show that TTFields application leads to a decrease in cyclin D1 protein levels.

FIG. 15 shows the combination of TTFields with Src inhibitor on colonogenicity.

DETAILED DESCRIPTION

Figure 1:
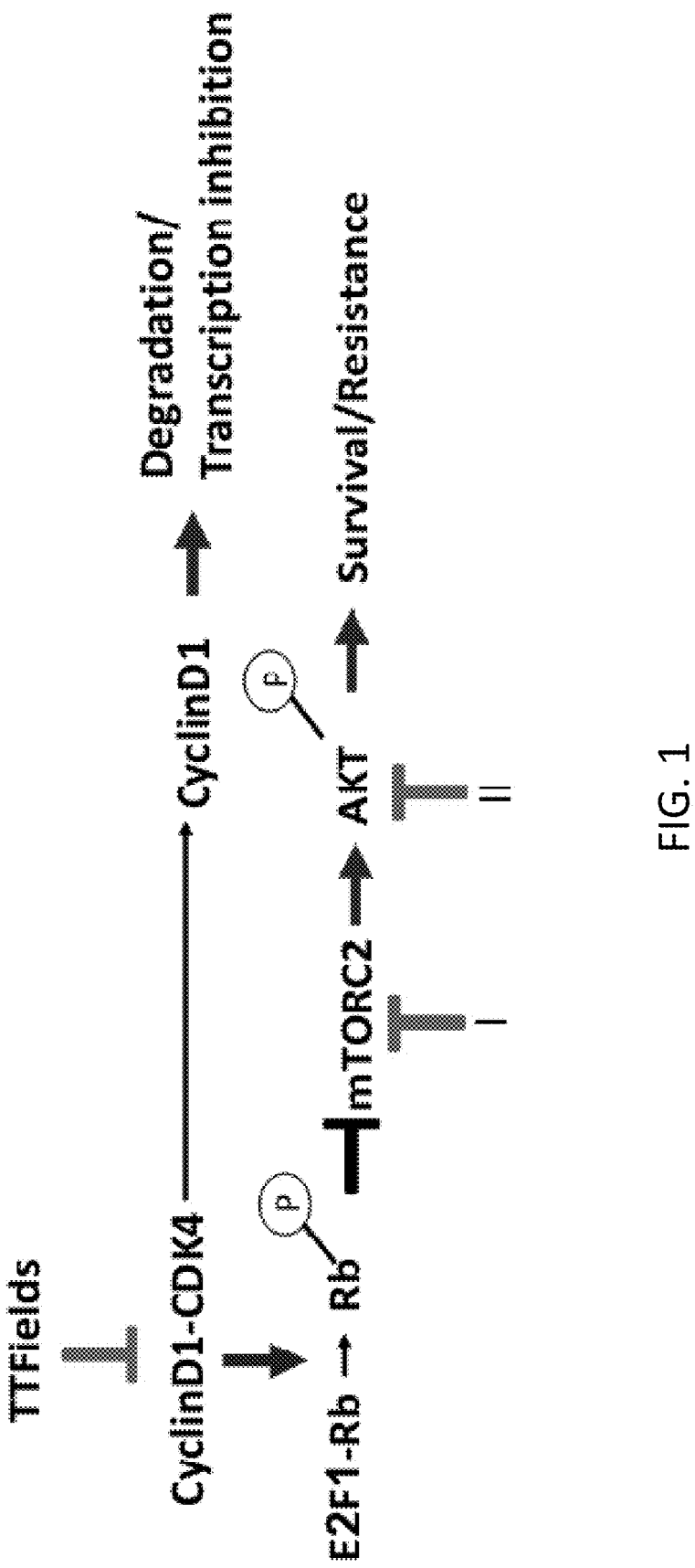
FIG. 1 shows a schematic representation of pathway.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a mTOR inhibitor" or "an mTOR inhibitor" includes a plurality of such mTOR inhibitors, reference to "the cancer cell" is a reference to one or more cancer cells and equivalents thereof known to those skilled in the art, and so forth.

As used herein, an "alternating electric field" or "alternating electric fields" refers to a very-low-intensity, directional, intermediate-frequency alternating electrical fields delivered to a subject, a sample obtained from a subject or to a specific location within a subject or patient (e.g. a target site). In some aspects, the alternating electrical field can be in a single direction or multiple directional. In some aspects, alternating electric fields can be delivered through two pairs of transducer arrays that generate perpendicular fields within the treated heart. For example, for the Optune™ system (an alternating electric fields delivery system) one pair of electrodes is located to the left and right (LR) of the heart, and the other pair of electrodes is located anterior and posterior (AP) to the heart. Cycling the field between these two directions (i.e., LR and AP) ensures that a maximal range of cell orientations is targeted. In some aspects, an alternating electric fields can be referred to as Tumor Treating Fields (TTFs).

In-vivo and in-vitro studies show that the efficacy of alternating electric fields therapy increases as the intensity of the electrical field increases. Therefore, optimizing array placement on the area of a patient's tumor to increase the intensity in the desired region of the tumor can be performed with the Optune system. Array placement optimization may be performed by "rule of thumb" (e.g., placing the arrays on the tumor as close to the desired region of the target site (e.g. cancer cells) as possible), measurements describing the geometry of the patient's tumor, tumor dimensions. Measurements used as input may be derived from imaging data. Imaging data is intended to include any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electrical field distributes within the head as a function of the positions of the array and, in some aspects, take account for variations in the electrical property distributions within the heads of different patients.

The term "subject" refers to the target of administration, e.g. an animal. Thus, the subject of the disclosed methods can be a vertebrate, such as a mammal. For example, the subject can be a human. The term does not denote a particular age or sex. Subject can be used interchangeably with "individual" or "patient." For example, the subject of administration can mean the recipient of the alternating electrical fields.

By "treat" is meant to administer or apply a therapeutic, such as alternating electric fields, to a subject, such as a human or other mammal (for example, an animal model), that has cancer or has an increased susceptibility for developing cancer, in order to prevent or delay a worsening of the effects of the cancer, or to partially or fully reverse the effects of the cancer (glioblastoma, ovarian, or lung metastatic carcinoma).

By "prevent" is meant to minimize the chance that a subject who has an increased susceptibility for developing cancer will develop cancer.

As used herein, the terms "administering" and "administration" refer to any method of providing a therapeutic, such as a mTOR inhibitor, AKT inhibitor, PI3K inhibitor, Src inhibitor, Fak inhibitor, or GSK3β inhibitor to a subject. Such methods are well known to those skilled in the art and include, but are not limited to: oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration so as to treat a subject. In some aspects, administering comprises exposing. Thus, in some aspects, exposing a cancer cell to alternating electrical fields means administering alternating electrical fields to the cancer cell.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Methods of Increasing Sensitivity

In some aspects, an active cyclin D1 pathway results in reduced or no cell survival. As shown in FIG. 1, cyclin D1 can form a complex to become cyclin D1-CDK4 which triggers the release and phosphorylation of Retinoblastoma tumor suppressor protein (Rb) from an E2F1-Rb complex. Phosphorylated Rb inhibits mTORC2 and therefore AKT is not phosphorylated which prevents cell survival. Based on this pathway, a decrease in cyclin D1 can result in little to no Rb release and phosphorylation which results in active mTORC2. Active mTORC2 causes phosphorylation of AKT resulting in cell survival. Thus, in some aspects, alternating electric fields can cause a decrease in cyclin D1 which would increase cell survival, the opposite effect intended by the alternating electric fields.

In some aspects, cancer cells can be treated with alternating electric fields to help kill the cell by disrupting the division of the cancer cell. However, in some aspects, alternating electric fields can cause a decrease in cyclin D1 which would increase cell survival, the opposite effect intended by the alternating electric fields. Thus, disclosed herein are methods for increasing sensitivity of a cancer cell to alternating electric fields by altering the cyclin D1 pathway. Also, disclosed herein are methods for increasing sensitivity of a cancer cell to alternating electric fields by administering a mTOR inhibitor, AKT inhibitor, PI3K inhibitor, Src inhibitor, Fak inhibitor, and/or GSK3β inhibitor.

Disclosed are methods of increasing sensitivity of a cancer cell to alternating electric fields comprising exposing the cancer cell to alternating electric fields for a period of time, the alternating electric fields having a frequency and field strength, wherein the frequency and field strength of the alternating electric field, and exposing the cancer cell to an mTOR inhibitor, AKT inhibitor, PI3K inhibitor, Src inhibitor, Fak inhibitor, and/or GSK3β inhibitor. In some aspects, the mTOR inhibitor is an mTORC2 inhibitor. In some aspects, the mTOR inhibitor can be selected from, but is not limited to, one or more of the group consisting of: torkinibs, everolimus, temsirolimus, everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D or TML-6.

In some aspects, an AKT inhibitor can be any composition or compound that inhibits AKT, inhibits phosphorylation of AKT, inhibits phosphorylated AKT, or inhibits degradation of cyclinD1. In some aspects, an AKT inhibitor can be, but is not limited to, lapatinib, H8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363, ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazo 1,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, or Scutellarin.

In some aspects, PI3K results in phosphorylation of AKT and cell survival. Thus, also disclosed are methods of increasing sensitivity of a cancer cell to alternating electric fields comprising exposing the cancer cell to alternating electric fields for a period of time, the alternating electric fields having a frequency and field strength, wherein the frequency and field strength of the alternating electric field, and exposing the cancer cell to a PI3K inhibitor. Because the alternating electric fields can decrease cyclin D1 which leads to an increase in phosphorylated AKT and an increase in cell survival, the addition of a PI3K which prevents AKT phosphorylation and results in reduced cell survival can be an effective combination treatment with alternating electric fields. In some aspects, a PI3K inhibitor can be a PI3K and mTOR dual inhibitor. In some aspects, the PI3K inhibitor can be, but is not limited to, GDC-0941, TG100-115, CH5132799, PX-866, XL147, ZSTK474, BKM-120, BAY80-6946, AZD8835, WX-037, AZD8186, KA2237, CAL-120, ME401, AMG319, GSK2636771, INCB050465, INK-1117, TGR-1202, RP6530, GDC-0032, BYL719, IPI-145, CAL-101, AMG511, ADZ6482, MLN1117, 3-Hydroxyanthranilic acid, Hispidulin, Pectolinarin, or Cinobufagin.

In some aspects, GSK3β results in phosphorylation of AKT and cell survival. Thus, also disclosed are methods of increasing sensitivity of a cancer cell to alternating electric fields comprising exposing the cancer cell to alternating electric fields for a period of time, the alternating electric fields having a frequency and field strength, wherein the frequency and field strength of the alternating electric fields, and exposing the cancer cell to a GSK3β inhibitor. In some aspects, the GSK3β inhibitor can be, but is not limited to, Lithium, Zinc, Tungstate, Naproxen, Cromolyn, Famotidine, Olanzapine, Pyrimidine derivatives, CT98014, CT98023, CT99021, TWS119, Indirubine, 6-BIO, Hymenialdisine, Dibromocanthareline, Meridianin, Arylindolemaleimide, SB-216763, SB-41528, Thiazoles, AR-A014418, AZD-1080, Paullones, Kenpaullone, Alsterpaullone, Cazpaullone, Alosines, Manzamins, Manzamin A, Furanosesquiterpenes, Palinurine, Tricantine, L803-mts, Thiadiazolidindiones, TDZD-8, NP00111, NP031115, NP031112 (tideglusib), Halomethylketones (HMK-32), L803-mts, CH1R99021, CT99021, TWS119, Aloisines, 9-ING-41, 1-Azakenpaullone, IM-12, CHIR-98014, or LY2090314.

In some aspects, Src inhibitors can be used in combination with alternating electric fields. Examples of src inhibitors include, but are not limited to, Dasatinib (BMS-354825), Ponatinib (AP24534), Saracatinib (AZD0530), Bosutinib (SKI-606), Dehydroabietic acid (DAA, DHAA), PP2, Ginkgolic acid C17:1 (GAC 17:1), DGY-06-116, Doramapimod (BIRB 796), Apatinib, Pelitinib (EKB-569), Resveratrol, KX2-391 (Tirabanibulin), NVP-BHG712, ENMD-2076, PRT062607 (P505-15, BIIB057, PRT-2607), PP1, MNS(3,4 Methylenedioxy-β-nitrostyrene), Doramapimod (BIRB 796), WH-4-023, RK24466, KX1-004, 7-Hydroxychromone, AD-80. Repotrectinib (TPX-0005), Quercetin (NSC 9221, Sophoretin, C.I. 75720), SU 6656, Src Inhibitor 1 (CAS 179248-59-0), CCT196969, Myristic acid (Tetradecanoic acid), eCF506, 1-Naphthyl PP1(1-NA-PP 1), AMG-47a. ON123300, UM-164, MLR-1023, PD173955, AZD0424, PD180970 or HG-7-85-01.

In some aspects, Fak inhibitors can be used in combination with alternating electric fields. Examples of Fak inhibitors include, but are not limited to Defectanib (VS-6063), Solanesol (nonaisoprenol), PF-00562271 Besylate (PF-562271), PF-562271 (PF-00562271), PRT062607 (P505-15, BIIB057, PRT-2607), PF-573228 TAE226 (NVP-TAE226), PF-562271 HCl, BI-4464, Y15, GSK2256098, PND-1186 (VS-4718), PF-431396, FAK inhibitor 14 (cas 4506-66-5) or Rebastinib.

In some aspects, the cancer cell is a glioblastoma cell, ovarian cell, or lung metastatic carcinoma cell. In some aspects, the cancer cell can be from any cancer.

In some aspects, the cancer cell is in a subject. Thus, in some aspects, exposing the cancer cell to alternating electric fields for a period of time comprises applying the alternating electric fields to the subject in an area comprising the cancer cells. For example, if the cancer cell is a glioblastoma cell then the alternating electric fields can be applied to the head of the subject.

In some aspects, the cancer cells are exposed to the alternating electric fields and mTOR inhibitor or AKT inhibitor simultaneously. In some aspects, the cancer cells are exposed to the alternating electric fields and PI3K inhibitor simultaneously. In some aspects, the cancer cells are exposed to the alternating electric fields and PI3K inhibitor simultaneously.

In some aspects, the disclosed methods can further comprise increasing cyclin D1 protein expression in the cancer cell. In some aspects, increasing cyclin D1 protein expression can mean restoring or partially restoring cyclin D1 to levels prior to exposing to the alternating electric fields. Cyclin D1 protein expression can be increased by administering recombinant cyclin D1 to the cells or administering a transcription activator that upregulates cyclin D1 mRNA. In some aspects, restoring or partially restoring cyclin D1 to levels prior to exposing to the alternating electric fields can be achieved by measuring cyclin D1 levels prior to exposing to the alternating electric fields and then monitoring levels after exposing to the alternating electric fields and administering recombinant cyclin D1 or administering a transcription activator that upregulates cyclin D1 mRNA to the cells until levels are restored or partially restored to levels prior to exposing to the alternating electric fields. In some aspects, restoring or partially restoring cyclin D1 to levels prior to exposing to the alternating electric fields can be based on a standard range of normal cyclin D1 levels in a subject of that age range. As used herein, the phrase "partially restore" or "partially restoring" refers to restoring cyclin D1 levels to levels below where they started prior to exposing to the alternating electric fields. In some aspects, partially restored levels can be 95%, 90%, 85%, 80%, 75%, 70%, 65%, 60%, 55%, 50%, or lower than where the cyclin D1 levels started prior to exposing to the alternating electric fields.

In some aspects, the cancer cells are exposed to the alternating electric fields just prior to, simultaneously, or just after cyclin D1 protein expression is restored. In some aspects, the cancer cells are exposed to the alternating electric fields, and the mTOR inhibitor, AKT inhibitor, PI3K inhibitor, src inhibitor, Fak inhibitor, or GSK3β inhibitor just prior to, simultaneously with, or just after cyclin D1 protein expression is restored.

Disclosed are any of the above methods of increasing sensitivity of a cancer cell to alternating electric fields comprising exposing the cancer cell to alternating electric fields for a period of time, the alternating electric fields having a frequency and field strength, wherein the frequency and field strength of the alternating electric fields, and exposing the cancer cell to an mTOR inhibitor, AKT inhibitor, PI3K inhibitor, src inhibitor, Fak inhibitor, and/or GSK3β inhibitor further comprising exposing the cell to a chemotherapeutic agent. In some aspects, a chemotherapeutic agent can be, but is not limited to, an alkylating agent, an antimetabolite agent, an antineoplastic antibiotic agent, a mitotic inhibitor agent. In some aspects, the methods can further comprise exposing a cell to radiation therapy. In some aspects, the methods can further comprise exposing a cell to an immuno-oncology agent. In some aspects, an immune-oncology agent can be, but is not limited to, immune checkpoint inhibitors such as, Ipilimumab, Nivolumab, Pembrolizumab, Atezolizumab, Avelumab, and Durvalumab. In some aspects, these categories of agents and therapeutics are overlapping, for example, Pebrolizumab is an immune-oncology agent and also considered an antineoplastic agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

C. Methods of Treating

Disclosed are methods of increasing treatment efficacy comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor to the subject.

Disclosed are methods of treating a subject having cancer comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor to the subject.

In some aspects, the one or more of the mTOR inhibitor, AKT inhibitor, PI3K inhibitor, Src inhibitor, Fak inhibitor, or GSK3β inhibitor is administered prior to applying the alternating electric fields. In some aspects, the one or more of the mTOR inhibitor, AKT inhibitor, PI3K inhibitor, Src inhibitor, Fak inhibitor, or GSK3β inhibitor is administered after applying the alternating electric fields. In some aspects, the one or more of the mTOR inhibitor, AKT inhibitor, PI3K inhibitor, Src inhibitor, Fak inhibitor, or GSK3β inhibitor is administered simultaneously with applying the alternating electric field.

In some aspects, the cancer is a glioblastoma, ovarian, or lung metastatic carcinoma. In some aspects, the cancer can be any cancer.

In some aspects, the mTOR inhibitor is an mTORC2 inhibitor. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D and TML-6.

In some aspects, an AKT inhibitor can be any composition or compound that inhibits AKT, inhibits phosphorylation of AKT, inhibits phosphorylated AKT, or inhibits degradation of cyclinD1. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363 (Capivasertib), ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazo 1,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin Resibfogenin, Terameprocol, Oroxin B, LM22B-10, Amarogentin, Oridonin, Praeruptorin A, Scutellarin, GNE-317, GNE-403, or NSC781406.

In some aspects, a PI3K inhibitor can be a PI3K and mTOR dual inhibitor. In some aspects, the PI3K inhibitor can be, but is not limited to DS-7423, PF-04691502, PKI-179, GSK458V, P7170, SB2343, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, BEZ235, GDC-0084, GDC-0980, LY3023414, PQR309, XL765, SF-1126, PF-05212384, or PKI-587. In some aspects, the PI3K inhibitor can be, but is not limited to, GDC-0941, TG100-115, CH5132799, PX-866, XL147, ZSTK474, BKM-120, BAY80-6946, AZD8835, WX-037, AZD8186, KA2237, CAL-120, ME401, AMG319, GSK2636771, INCB050465, INK-1117, TGR-1202, RP6530, GDC-0032, BYL719, IPI-145, CAL-101, AMG511, ADZ6482, MLN1117, 3-Hydroxyanthranilic acid, Hispidulin, Pectolinarin, or Cinobufagin.

In some aspects, the GSK3β inhibitor can be, but is not limited to, Lithium, Zinc, Tungstate, Naproxen, Cromolyn, Famotidine, Olanzapine, Pyrimidine derivatives, CT98014, CT98023, CT99021, TWS119, Indirubine, 6-BIO, Hymenialdisine, Dibromocanthareline, Meridianin, Arylindolemaleimide, SB-216763, SB-41528, Thiazoles, AR-A014418, AZD-1080, Paullones, Kenpaullone, Alsterpaullone, Cazpaullone, Alosines, Manzamins, Manzamin A, Furanosesquiterpenes, Palinurine, Tricantine, L803-mts, Thiadiazolidindiones, TDZD-8, NP00111, NP031115, NP031112 (tideglusib), Halomethylketones (HMK-32), L803-mts, CH1R99021, CT99021, TWS119, Aloisines, 9-ING-41, 1-Azakenpaullone, IM-12, CHIR-98014 or LY2090314.

In some aspects, Src inhibitors can be, but are not limited to, Dasatinib (BMS-354825), Ponatinib (AP24534), Saracatinib (AZD0530), Bosutinib (SKI-606), Dehydroabietic acid (DAA, DHAA), PP2, Ginkgolic acid C17:1 (GAC 17:1), DGY-06-116, Doramapimod (BIRB 796), Apatinib, Pelitinib (EKB-569), Resveratrol, KX2-391 (Tirabanibulin), NVP-BHG712, ENMD-2076, PRT062607 (P505-15, BIIB057, PRT-2607), PP1, MNS(3,4 Methylenedioxy-β-nitrostyrene), Doramapimod (BIRB 796), WH-4-023, RK24466, KX1-004, 7-Hydroxychromone, AD-80. Repotrectinib (TPX-0005), Quercetin (NSC 9221, Sophoretin, C.I. 75720), SU 6656, Src Inhibitor 1 (CAS 179248-59-0), CCT196969, Myristic acid (Tetradecanoic acid), eCF506, 1-Naphthyl PP1(1-NA-PP 1), AMG-47a. ON123300, UM-164, MLR-1023.PD173955, AZD0424, PD180970 or HG-7-85-01.

In some aspects, FAK inhibitors can be, but are not limited to, Defectanib (VS-6063), Solanesol (nonaisoprenol), PF-00562271 Besylate (PF-562271), PF-562271 (PF-00562271), PRT062607 (P505-15, BIIB057, PRT-2607), PF-573228 TAE226 (NVP-TAE226), PF-562271 HCl, BI-4464, Y15, GSK2256098, PND-1186(VS-4718), PF-431396, FAK inhibitor 14 (cas 4506-66-5) or Rebastinib.

In some aspects, the alternating electric fields decreases cyclin D1 protein levels in the one or more cancer cells.

In some aspects, the disclosed methods can further comprise increasing cyclin D1 protein expression in the subject, in particular in the cancer cells of the subject. In some aspects, increasing cyclin D1 protein expression can mean restoring or partially restoring cyclin D1 to levels prior to exposing to the alternating electric fields. Cyclin D1 protein expression can be increased by administering recombinant cyclin D1 to the cells or administering a transcription activator that upregulates cyclin D1 mRNA. In some aspects, restoring or partially restoring cyclin D1 to levels prior to exposing to the alternating electric fields can be achieved by measuring cyclin D1 levels prior to exposing to the alternating electric fields and then monitoring levels after exposing to the alternating electric fields and administering recombinant cyclin D1 or administering a transcription activator that upregulates cyclin D1 mRNA to the cells until levels are restored or partially restored to levels prior to exposing to the alternating electric fields. In some aspects, restoring or partially restoring cyclin D1 to levels prior to exposing to the alternating electric fields can be based on a standard range of normal cyclin D1 levels in a subject of that age range. As used herein, the phrase "partially restore" or "partially restoring" refers to restoring cyclin D1 levels to levels below where they started prior to exposing to the alternating electric fields. In some aspects, partially restored levels can be 95%, 90%, 85%, 80%, 75%, 70%, 65%, 60%, 55%, 50%, or lower than where the cyclin D1 levels started prior to exposing to the alternating electric fields.

In some aspects, the disclosed methods of increasing treatment efficacy comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor in combination with radiation therapy to the subject, wherein the result is an increase in cell susceptibility to DNA damage from the radiation therapy.

In some aspects, disclosed are methods comprising administering one or more of an mTOR inhibitor, AKT inhibitor, PI3K inhibitor, Src inhibitor, Fak inhibitor, or GSK3β inhibitor in combination with alternating electric fields in order to decrease BRCA expression due to the release of E2F1 from the EFF1-Rb complex.

Disclosed are any of the above methods of increasing treatment efficacy or methods of treating a subject having cancer comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor to the subject, and further comprising administering a chemotherapeutic agent to the subject. In some aspects, a chemotherapeutic agent can be, but is not limited to, an alkylating agent, an antimetabolite agent, an antineoplastic antibiotic agent, and a mitotic inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

D. Methods of Reducing Viability of Cancer Cells

Disclosed are methods of reducing viability of cancer cells using alternating electric fields for a period of time, the alternating electric fields having a frequency and field strength in combination with either an mTOR inhibitor, AKT inhibitor, PI3K inhibitor, Src inhibitor, Fak inhibitor, or GSK3β inhibitor and/or a composition or compound that increases cyclin D1.

Also disclosed are methods of reducing viability of cancer cells using alternating electric fields for a period of time, the alternating electric fields having a frequency and field strength in combination with either an mTOR inhibitor, AKT inhibitor, PI3K inhibitor, Src inhibitor, Fak inhibitor, or GSK3β inhibitor and/or a composition or compound that increases cyclin D1, and further comprising administering a chemotherapeutic agent to the subject. In some aspects, a chemotherapeutic agent can be, but is not limited to, an alkylating agent, an antimetabolite agent, an antineoplastic antibiotic agent, and a mitotic inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

1. Alternating Electric Fields Plus Inhibitor

Disclosed are methods of reducing viability of cancer cells comprising applying alternating electric fields to a target site of the subject for a period of time, the alternating electric fields having a frequency and field strength, wherein the target site comprises one or more cancer cells, and administering a therapeutically effective amount of one or more of an mTOR inhibitor, AKT inhibitor, PI3K inhibitor, Src inhibitor, Fak inhibitor, or GSK3β inhibitor to the subject.

In some aspects, the one or more of the mTOR inhibitor, AKT inhibitor, PI3K inhibitor, Src inhibitor, Fak inhibitor, or GSK3β inhibitor is administered prior to applying the alternating electric fields. In some aspects, the one or more of the mTOR inhibitor, AKT inhibitor, PI3K inhibitor, Src inhibitor, Fak inhibitor, or GSK3β inhibitor is administered after applying the alternating electric fields. In some aspects, the one or more of the mTOR inhibitor, AKT inhibitor, PI3K inhibitor, Src inhibitor, Fak inhibitor, or GSK3β inhibitor is administered simultaneously with applying the alternating electric fields.

In some aspects, the cancer is a glioblastoma, ovarian, or lung metastatic carcinoma. In some aspects, the cancer can be any cancer.

In some aspects, the mTOR inhibitor is an mTORC2 inhibitor. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523 mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D or TML-6.

In some aspects, an AKT inhibitor can be any composition or compound that inhibits AKT, inhibits phosphorylation of AKT, inhibits phosphorylated AKT, or inhibits degradation of cyclinD1. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363, ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazo 1,2 pyridine derivatives), Rigosertib (ON-01910), Triciribine, Honokiol, Miransertib (ARQ 092), Borussertib, SC66 A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, or Scutellarin.

In some aspects, a PI3K inhibitor can be a PI3K and mTOR dual inhibitor. In some aspects, the PI3K inhibitor can be, but is not limited to DS-7423, PF-04691502, PKI-179, GSK458V, P7170, SB2343, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, BEZ235, GDC-0084, GDC-0980, LY3023414, PQR309, XL765, SF-1126, PF-05212384, or PKI-587. In some aspects, the PI3K inhibitor can be, but is not limited to, GDC-0941, TG100-115, CH5132799, PX-866, XL147, ZSTK474, BKM-120, BAY80-6946, AZD8835, WX-037, AZD8186, KA2237, CAL-120, ME401, AMG319, GSK2636771, INCB050465, INK-1117, TGR-1202, RP6530, GDC-0032, BYL719, IPI-145, CAL-101, AMG511, ADZ6482, MLN1117, 3-Hydroxyanthranilic acid, Hispidulin, Pectolinarin, or Cinobufagin.

In some aspects, the src inhibitor can be, but is not limited to, Dasatinib (BMS-354825), Ponatinib (AP24534), Saracatinib (AZD0530), Bosutinib (SKI-606), Dehydroabietic acid (DAA, DHAA), PP2, Ginkgolic acid C17:1 (GAC 17:1), DGY-06-116, Doramapimod (BIRB 796), Apatinib, Pelitinib (EKB-569), Resveratrol, KX2-391 (Tirabanibulin), NVP-BHG712, ENMD-2076, PRT062607 (P505-15, BIIB057, PRT-2607), PP1, MNS(3,4 Methylenedioxy-β-nitrostyrene), Doramapimod (BIRB 796), WH-4-023, RK24466, KX1-004, 7-Hydroxychromone, AD-80. Repotrectinib (TPX-0005), Quercetin (NSC 9221, Sophoretin, C.I. 75720), SU 6656, Src Inhibitor 1 (CAS 179248-59-0), CCT196969, Myristic acid (Tetradecanoic acid), eCF506, 1-Naphthyl PP1(1-NA-PP 1), AMG-47a. ON123300, UM-164, MLR-1023.PD173955, AZD0424, PD180970 or HG-7-85-01.

In some aspects, the Fak inhibitor can be, but is not limited to, Defectanib (VS-6063), Solanesol (nonaisoprenol), PF-00562271 Besylate (PF-562271), PF-562271 (PF-00562271), PRT062607 (P505-15, BIIB057, PRT-2607), PF-573228 TAE226 (NVP-TAE226), PF-562271 HCl, BI-4464, Y15, GSK2256098, PND-1186(VS-4718), PF-431396, FAK inhibitor 14 (cas 4506-66-5) or Rebastinib.

In some aspects, the GSK3β inhibitor can be, but is not limited to, Lithium, Zinc, Tungstate, Naproxen, Cromolyn, Famotidine, Olanzapine, Pyrimidine derivatives, CT98014, CT98023, CT99021, TWS119, Indirubine, 6-BIO, Hymenialdisine, Dibromocanthareline, Meridianin, Arylindolemaleimide, SB-216763, SB-41528, Thiazoles, AR-A014418, AZD-1080, Paullones, Kenpaullone, Alsterpaullone, Cazpaullone, Alosines, ManzaminsManzamin A, Furanosesquiterpenes, Palinurine, Tricantine, L803-mts, Thiadiazolidindiones, TDZD-8, NP00111, NP031115, NP031112(tideglusib), Halomethylketones (HMK-32), L803-mts, CH1R99021, CT99021, TWS119, Aloisines, 9-ING-41, 1-Azakenpaullone, IM-12, CHIR-98014 or LY2090314.

In some aspects, the alternating electric fields decreases cyclin D1 protein levels in the one or more cancer cells.

In some aspects, the disclosed methods can further comprise increasing cyclin D1 protein expression in the subject, in particular in the cancer cells of the subject. In some aspects, increasing cyclin D1 protein expression can mean restoring or partially restoring cyclin D1 to levels prior to exposing to the alternating electric fields. Cyclin D1 protein expression can be increased by administering recombinant cyclin D1 to the cells or administering a transcription activator that upregulates cyclin D1 mRNA. In some aspects, restoring or partially restoring cyclin D1 to levels prior to exposing to the alternating electric fields can be achieved by measuring cyclin D1 levels prior to exposing to the alternating electric fields and then monitoring levels after exposing to the alternating electric fields and administering recombinant cyclin D1 or administering a transcription activator that upregulates cyclin D1 mRNA to the cells until levels are restored or partially restored to levels prior to exposing to the alternating electric fields. In some aspects, restoring or partially restoring cyclin D1 to levels prior to exposing to the alternating electric fields can be based on a standard range of normal cyclin D1 levels in a subject of that age range. As used herein, the phrase "partially restore" or "partially restoring" refers to restoring cyclin D1 levels to levels below where they started prior to exposing to the alternating electric fields. In some aspects, partially restored levels can be 95%, 90%, 85%, 80%, 75%, 70%, 65%, 60%, 55%, 50%, or lower than where the cyclin D1 levels started prior to exposing to the alternating electric fields.

2. Alternating Electric Fields Plus Increasing Cyclin D1

In some aspects, disclosed are methods of reducing viability of cancer cells comprising exposing the cancer cell to alternating electric fields for a period of time, the alternating electric fields having a frequency and field strength; and upregulating or increasing cyclin D1 protein expression in the cancer cell, thereby reducing the viability of the cancer cell.

In some aspects, the methods of reducing viability of cancer cells comprising exposing the cancer cell to alternating electric fields for a period of time, the alternating electric fields having a frequency and field strength; and upregulating or increasing cyclin D1 protein expression in the cancer cell, thereby reducing the viability of the cancer cell can further comprise exposing the cancer cell to one or more of a mTOR inhibitor, AKT inhibitor, PI3K inhibitor, Src inhibitor, Fak inhibitor, or GSK3β inhibitor.

In some aspects, the cancer cell is in a subject. Thus, in some aspects, exposing the cancer cell to alternating electric fields for a period of time comprises applying the alternating electric fields to the subject in an area comprising the cancer cells. For example, if the cancer cell is a glioblastoma cell then the alternating electric fields can be applied to the head of the subject.

In some aspects, the one or more of the mTOR inhibitor, AKT inhibitor, PI3K inhibitor, Src inhibitor, Fak inhibitor, or GSK3β inhibitor is administered prior to applying the alternating electric fields. In some aspects, the one or more of the mTOR inhibitor, AKT inhibitor, PI3K inhibitor, Src inhibitor, Fak inhibitor, or GSK3β inhibitor is administered after applying the alternating electric fields. In some aspects, the one or more of the mTOR inhibitor, AKT inhibitor, PI3K inhibitor, Src inhibitor, Fak inhibitor, or GSK3β inhibitor is administered simultaneously with applying the alternating electric fields.

In some aspects, the cancer is a glioblastoma, ovarian, or lung metastatic carcinoma. In some aspects, the cancer can be any cancer.

In some aspects, the mTOR inhibitor is an mTORC2 inhibitor. In some aspects, the mTOR inhibitor can be selected from, but is not limited to, one or more of the group consisting of: torkinibs, everolimus, temsirolimus, (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usnic acid, RMC-5552, PRQ530, JR-AB2-011, Arnicolide D or TML-6.

In some aspects, an AKT inhibitor can be any composition or compound that inhibits AKT, inhibits phosphorylation of AKT, inhibits phosphorylated AKT, or inhibits degradation of cyclinD1. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363, ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazo 1,2 pyridine derivatives), Rigosertib (ON-01910), Triciribine, Honokiol, Miransertib (ARQ 092), Borussertib, SC66 A-674563, TIC10 analogue, Urolithin B, ABTL-0821, Loureirin A, Homosalate, Deguelin, Resibfogenin, Teramcprocol, Oroxin B, LM22B-10, Amarogentin, Oridonin, Praeruptorin A, or Scutellarin.

In some aspects, a PI3K inhibitor can be a PI3K and mTOR dual inhibitor. In some aspects, the PI3K inhibitor can be, but is not limited to, DS-7423, PF-04691502, PKI-179, GSK458V, P7170, SB2343, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, BEZ235, GDC-0084, GDC-0980, LY3023414, PQR309, XL765, SF-1126, PF-05212384, or PKI-587. In some aspects, the PI3K inhibitor can be, but is not limited to, GDC-0941, TG100-115, CH5132799, PX-866, XL147, ZSTK474, BKM-120, BAY80-6946, AZD8835, WX-037, AZD8186, KA2237, CAL-120, ME401, AMG319, GSK2636771, INCB050465, INK-1117, TGR-1202, RP6530, GDC-0032, BYL719, IPI-145, CAL-101, AMG511, ADZ6482, MLN1117, 3-Hydroxyanthranilic acid, Hispidulin, Pectolinarin, or Cinobufagin.

In some aspects, the GSK3β inhibitor can be, but is not limited to, Lithium, Zinc, Tungstate, Naproxen, Cromolyn, Famotidine, Olanzapine, Pyrimidine derivatives, CT98014, CT98023, CT99021, TWS119, Indirubine, 6-BIO, Hymenialdisine, Dibromocanthareline, Meridianin, Arylindolemaleimide, SB-216763, SB-41528, Thiazoles, AR-A014418, AZD-1080, Paullones, Kenpaullone, Alsterpaullone, Cazpaullone, Alosines, Manzamins, Manzamin A, Furanosesquiterpenes, Palinurine, Tricantine, L803-mts, Thiadiazolidindiones, TDZD-8, NP00111, NP031115, NP031112(tideglusib), Halomethylketones (HMK-32), L803-mts, CH1R99021, CT99021, TWS119, Aloisines, 9-ING-41, 1-Azakenpaullone, IM-12, CHIR-98014 or LY2090314.

In some aspects, the src inhibitor can be, but is not limited to, Dasatinib (BMS-354825), Ponatinib (AP24534), Saracatinib (AZD0530), Bosutinib (SKI-606), Dehydroabietic acid (DAA, DHAA), PP2, Ginkgolic acid C17:1 (GAC 17:1), DGY-06-116, Doramapimod (BIRB 796), Apatinib, Pelitinib (EKB-569), Resveratrol, KX2-391 (Tirabanibulin), NVP-BHG712, ENMD-2076, PRT062607 (P505-15, BIIB057, PRT-2607), PP1, MNS(3,4 Methylenedioxy-β-nitrostyrene), Doramapimod (BIRB 796), WH-4-023, RK24466, KX1-004, 7-Hydroxychromone, AD-80. Repotrectinib (TPX-0005), Quercetin (NSC 9221, Sophoretin, C.I. 75720), SU 6656, Src Inhibitor 1 (CAS 179248-59-0), CCT196969, Myristic acid (Tetradecanoic acid), eCF506, 1-Naphthyl PP1(1-NA-PP 1), AMG-47a. ON123300, UM-164, MLR-1023.PD173955, AZD0424, PD180970 or HG-7-85-01.

In some aspects, FAK inhibitors can be, but are not limited to, Defectanib (VS-6063), Solanesol (nonaisoprenol), PF-00562271 Besylate (PF-562271), PF-562271 (PF-00562271), PRT062607 (P505-15, BIIB057, PRT-2607), PF-573228 TAE226 (NVP-TAE226), PF-562271 HCl, BI-4464, Y15, GSK2256098, PND-1186(VS-4718), PF-431396, FAK inhibitor 14 (cas 4506-66-5) or Rebastinib.

In some aspects, the alternating electric fields decreases cyclin D1 protein levels in the one or more cancer cells.

In some aspects, the disclosed methods can further comprise increasing cyclin D1 protein expression in the subject, in particular in the cancer cells of the subject. In some aspects, increasing cyclin D1 protein expression can mean restoring or partially restoring cyclin D1 to levels prior to exposing to the alternating electric fields. Cyclin D1 protein expression can be increased by administering recombinant cyclin D1 to the cells or administering a transcription activator that upregulates cyclin D1 mRNA. In some aspects, restoring or partially restoring cyclin D1 to levels prior to exposing to the alternating electric fields can be achieved by measuring cyclin D1 levels prior to exposing to the alternating electric fields and then monitoring levels after exposing to the alternating electric fields and administering recombinant cyclin D1 or administering a transcription activator that upregulates cyclin D1 mRNA to the cells until levels are restored or partially restored to levels prior to exposing to the alternating electric fields. In some aspects, restoring or partially restoring cyclin D1 to levels prior to exposing to the alternating electric fields can be based on a standard range of normal cyclin D1 levels in a subject of that age range. As used herein, the phrase "partially restore" or "partially restoring" refers to restoring cyclin D1 levels to levels below where they started prior to exposing to the alternating electric fields. In some aspects, partially restored levels can be 95%, 90%, 85%, 80%, 75%, 70%, 65%, 60%, 55%, 50%, or lower than where the cyclin D1 levels started prior to exposing to the alternating electric fields.

E. Methods of Increasing Apoptosis

Disclosed are methods of increasing apoptosis of a cancer cell comprising exposing the cancer cell to alternating electric fields for a period of time, the alternating electric fields having a frequency and field strength; and exposing the cancer cell to a mTOR inhibitor, AKT inhibitor, PI3K inhibitor, and/or GSK3β inhibitor.

In some aspects, the PI3K inhibitor is a dual PI3K and mTOR inhibitor. For example, in some aspects, the PI3K and mTOR inhibitor is BGT226. In some aspects, the PI3K and mTOR inhibitor can be, but is not limited to, DS-7423, PF-04691502, PKI-179, GSK458V, P7170, SB2343, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, BEZ235, GDC-0084, GDC-0980, LY3023414, PQR309, XL765, SF-1126, PF-05212384, or PKI-587. In some aspects, the PI3K inhibitor can be, but is not limited to, GDC-0941, TG100-115, CH5132799, PX-866, XL147, ZSTK474, BKM-120, BAY80-6946, AZD8835, WX-037, AZD8186, KA2237, CAL-120, ME401, AMG319, GSK2636771, INCB050465, INK-1117, TGR-1202, RP6530, GDC-0032, BYL719, IPI-145, CAL-101, AMG511, ADZ6482, MLN1117, 3-Hydroxyanthranilic acid, Hispidulin, Pectolinarin, or Cinobufagin.

In some aspects, the mTOR inhibitor can be selected from, but is not limited to, one or more of the group consisting of: torkinibs, everolimus, temsirolimus, everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523 mTor inhibitor-1,2,3 or 8, PRQ626, WAY-600, PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D, or TML-6.

In some aspects, an AKT inhibitor can be any composition or compound that inhibits AKT, inhibits phosphorylation of AKT, inhibits phosphorylated AKT, or inhibits degradation of cyclinD1. In some aspects, an AKT inhibitor can be, but is not limited to, lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363, ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2

[4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazo 1,2 pyridine derivatives), Rigosertib (ON-01910), Triciribine, Honokiol, Miransertib (ARQ 092), Borussertib, SC66, A-674563, TIC10 analogue, Urolithin B, ABTL-0821, Loureirin A, Homosalate, Deguelin Resibfogenin, Terameprocol, Oroxin B, LM22B-10, Amarogentin, Oridonin, Praeruptorin A, or Scutellarin.

In some aspects, the GSK3β inhibitor can be, but is not limited to, Lithium, Zinc, Tungstate, Naproxen, Cromolyn, Famotidine, Olanzapine, Pyrimidine derivatives, CT98014, CT98023, CT99021, TWS119, Indirubine, 6-BIO, Hymenialdisine, Dibromocanthareline, Meridianin, Arylindolemaleimide, SB-216763, SB-41528, Thiazoles, AR-A014418, AZD-1080, Paullones, Kenpaullone, Alsterpaullone, Cazpaullone, Alosines, Manzamins, Manzamin A, Furanosesquiterpenes, Palinurine, Tricantine, L803-mts, Thiadiazolidindiones, TDZD-8, NP00111, NP031115, NP031112(tideglusib), Halomethylketones (HMK-32), L803-mts, CH1R99021, CT99021, TWS119, Aloisines, 9-ING-41, 1-Azakenpaullone, IM-12, CHIR-98014, or LY2090314.

In some aspects, a Src inhibitor can be, but is not limited to Dasatinib (BMS-354825), Ponatinib (AP24534), Saracatinib (AZD0530), Bosutinib (SKI-606), Dehydroabietic acid (DAA, DHAA), PP2, Ginkgolic acid C17:1 (GAC 17:1), DGY-06-116, Doramapimod (BIRB 796), Apatinib, Pelitinib (EKB-569), Resveratrol, KX2-391 (Tirabanibulin), NVP-BHG712, ENMD-2076, PRT062607 (P505-15, BIIB057, PRT-2607), PP1, MNS(3,4 Methylenedioxy-β-nitrostyrene), Doramapimod (BIRB 796), WH-4-023, RK24466, KX1-004, 7-Hydroxychromone, AD-80. Repotrectinib (TPX-0005), Quercetin (NSC 9221, Sophoretin, C.I. 75720), SU 6656, Src Inhibitor 1 (CAS 179248-59-0), CCT196969, Myristic acid (Tetradecanoic acid), eCF506, 1-Naphthyl PP1(1-NA-PP 1), AMG-47a. ON123300, UM-164, MLR-1023.PD173955, AZD0424, PD180970 or HG-7-85-01.

In some aspects, a FAK inhibitor can be, but is not limited to, Defactanib (VS-6063), Solanesol (nonaisoprenol), PF-00562271 Besylate (PF-562271), PF-562271 (PF-00562271), PRT062607 (P505-15, BIIB057, PRT-2607), PF-573228 TAE226 (NVP-TAE226), PF-562271 HCl, BI-4464, Y15, GSK2256098, PND-1186(VS-4718), PF-431396, FAK inhibitor 14 (cas 4506-66-5) or Rebastinib.

In some aspects, the alternating electric fields and the mTOR inhibitor, AKT inhibitor, PI3K inhibitor, Src inhibitor, Fak inhibitor, and/or GSK3β inhibitor are administered simultaneously. In some aspects, after simultaneous administration of alternating electric fields and the inhibitor, the inhibitor is removed while the cancer cells remain exposed to the alternating electric fields. In some aspects, even after the inhibitor is removed, the increase in apoptosis of cancer cells remains.

Disclosed are any of the above methods of increasing apoptosis of a cancer cell comprising exposing the cancer cell to alternating electric fields for a period of time, the alternating electric fields having a frequency and field strength; and exposing the cancer cell to a mTOR inhibitor, AKT inhibitor, PI3K inhibitor, Src inhibitor, Fak inhibitor, and/or GSK3β inhibitor and further comprising exposing the cell to a chemotherapeutic agent. In some aspects, a chemotherapeutic agent can be, but is not limited to, an alkylating agent, an antimetabolite agent, an antineoplastic antibiotic agent, and a mitotic inhibitor agent.

In a further aspect, the antineoplastic antibiotic agent is selected from doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the antimetabolite agent is selected from gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the alkylating agent is selected from carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the mitotic inhibitor agent is selected from irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

F. Alternating Electric Fields

The methods disclosed herein comprise alternating electric fields. In some aspects, the alternating electric fields used in the methods disclosed herein is a tumor-treating fields (TTFs). In some aspects, the alternating electric fields can vary dependent on the type of cell or condition to which the alternating electric fields are applied. In some aspects, the alternating electric fields can be applied through one or more electrodes placed on the subject's body. In some aspects, there can be two or more pairs of electrodes. For example, arrays can be placed on the front/back and sides of a patient and can be used with the systems and methods disclosed herein. In some aspects, where two pairs of electrodes are used, the alternating electric fields can alternate between the pairs of electrodes. For example, a first pair of electrodes can be placed on the front and back of the subject and a second pair of electrodes can be placed on either side of the subject, the alternating electric fields can then be applied and can alternate between the front and back electrodes and then to the side to side electrodes.

In some aspects, the frequency of the alternating electric fields is between 100 and 500 kHz. The frequency of the alternating electric fields can also be, but is not limited to, between 50 and 500 kHz, between 100 and 500 kHz, between 25 kHz and 1 MHz, between 50 and 190 kHz, between 25 and 190 kHz, between 180 and 220 kHz, or between 210 and 400 kHz. In some aspects, the frequency of the alternating electric fields can be electric fields at 50 kHz, 100 kHz, 200 kHz, 300 kHz, 400 kHz, 500 kHz, or any frequency between. In some aspects, the frequency of the alternating electric fields is from about 200 kHz to about 400 kHz, from about 250 kHz to about 350 kHz, and may be around 300 kHz.

In some aspects, the field strength of the alternating electric fields can be between 1 and 4 V/cm RMS. In some aspects, different field strengths can be used (e.g., between 0.1 and 10 V/cm). In some aspects, the field strength can be 1.75 V/cm RMS. In some embodiments the field strength is at least 1 V/cm. In other embodiments, combinations of field strengths are applied, for example combining two or more frequencies at the same time, and/or applying two or more frequencies at different times.

In some aspects, the alternating electric fields can be applied for a variety of different intervals ranging from 0.5 hours to 72 hours. In some aspects, a different duration can be used (e.g., between 0.5 hours and 14 days). In some aspects, application of the alternating electric fields can be repeated periodically. For example, the alternating electric fields can be applied every day for a two-hour duration.

In some aspects, the exposure may last for at least 6 hours, at least 12 hours, at least 24 hours, at least 36 hours, at least 48 hours, or at least 72 hours or more.

G. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits for treating cancer. In some aspects, the kit can comprise equipment for applying alternating electrical fields.

Also disclosed are kits comprising a system or equipment for administering alternating electrical fields and one or more of the disclosed mTOR inhibitor, AKT inhibitor, PI3K inhibitor, Src inhibitor, Fak inhibitor, or GSK3β inhibitor.

Examples

A. Materials and Methods

1. Cell Lines and Cultures

All cell lines were obtained from ATCC: U-87 (human glioma cell lines) and H1299 (human metastatic lung carcinoma), A2780 (ovarian cell line). Cells were cultured in Dulbecco's modified Eagle's medium (Biological Industries) or RPMI (GIBCO) medium supplemented with 5-10% fetal bovine serum and antibiotics.

5,000-50,000 single cells were suspended in 500 μL of media and seeded in the middle of a 22 mm diameter cover slip.

For induction of 24 hours or longer TTFields application the cover slips were placed in a ceramic dish of Inovitro™ system and allowed to incubate in a conventional tissue culture incubator (37° C., 95% air, 5% CO₂) overnight. Once cells adhered to the cover slip, an additional 1.5 mL of media were added to each well and covered in Parafilm (P7793, Sigma Aldrich) to avoid evaporation of media. After an overnight incubation dishes were mounted onto Inovitro™ base plates (Novocure Inc., Haifa, Israel). Tumor Treating electric fields set anywhere from 1-6 V/cm were applied through an Inovitro™ power generator while frequencies ranged from 50-500 kHz. Incubation temperature was 18° C. with a target temperature of 37° C. for the ceramic dishes upon application of the TTFields. Corresponding control experiments were done by placing equivalent cover slips within ceramic dishes into a conventional tissue culture incubator (37° C., 5% CO₂) and cells grown in parallel with the TTField-exposed coverslips.

2. Inhibitors

BGT226, Alpalisib, Pictilisib, BKM120 and Dasatinib were added was added to cells 12-24 hours after seeding for inhibitor mono-treatment and combination treatment to a final concentration of 8 nM, 1 nm, 1 nm, 500 nm and 75 nm respectively in A2780 cells. Control and TTFields samples received same volume of DMSO. Following 72 hours of treatment media was replaced for media with no inhibitor and cells were grown for additional 96 hours. At 168 hours (7 days) cytotoxic assay was performed by GentelMACS cell count, Apoptosis assay and cells were seeded for colony assay (as specified in cell count and Quantification of cell death).

3. Cell Lysates and Immunoblotting

Following TTFields application cells were transferred to cold PBS plates for wash.

RIPA lysis buffer (R0278, Sigma-Aldrich), supplemented with a cocktail of protease (Complete Mini, Roche), and phosphatase inhibitors (Halt #78420, Thermo Scientific) was added to plates and cells were scraped with approximately 100 μl supplemented RIPA buffer for 8 Inovitro™ dishes.

Extracts were shaken at 4° C. for a duration of 30 minutes. Samples were centrifuged (20 min, 14,000 rpm, 4° C.). supernatant was transferred and protein concentration was determined by BCA protein assay kit.

After determining protein concentration (BCA protein assay kit, ab102536 Abcam), 30 μg protein were resolved under reducing conditions (Bolt Sample reducing agent, #2060435 and Sample buffer #2045289, Novex) and samples were boiled at 100° C. for 5 minutes. Samples were run on SDS-polyacrylamide gel electrophoresis (Bolt 8% Bis-Tris base gel NW00080BOX, Thermo-Fischer).

After electrophoresis, proteins were transferred to 0.2 μm polyvinylidene difluoride membrane (Immuno-Blot PVDF #162-0177, Bio-Rad) and probed with the appropriate primary antibody: GAPDH (SC-32233, Santa Cruz), Vinculin (ab140007, Abcam), Cyclin D1 (2922, Cell Signaling), Rb (9309, Cell Signaling), pRb S807/811 (8516, Cell Signaling), pAkt 5473, (4051, Cell signaling), Akt (2920, Cell signaling)), FAK (3283S, Cell signaling), Phospho-FAK (Tyr397) (3283S, Cell signaling, Src (2109S, cell signaling) and Phospho-Src (Tyr416) (2101S, Cell signaling). followed by horseradish peroxidase-conjugated secondary antibody (goat anti rabbit 7074, Cell Signaling and goat anti mouse 7076, Cell Signaling) and a chemiluminescent substrate (WBLUF0100, Signa-Aldrich). Quantification of bands was done by Image J software.

4. Cell Count

Cells were detached from Inovitro™ dishes with 0.5 ml Trypsin A for approximately 5 minutes and then supplemented with 0.5 ml culture media. 200 μl of cells were taken to 96 well U-shaped plate to be counted in MACSQuant 10 flow cytometer. Analysis was performed with FlowJo_V10 software and statistics was done by GraphPad Prism 8 software.

5. Quantification of Cell Death

Cell death was assessed by double staining of cells with FITC-conjugated annexin V (MEBCYTO© 4700 Apoptosis Kit; MBL©) and 7-Aminoactinomycin D (7-AAD; BioLegend©) as per manufacturer's instructions.

Colony assay: following cell count 300 cells of each treatment were seeded in duplicates in 6 well dishes with 2 ml media. Once colonies were visible they were washed with PBS. Cells were fixed in −20° C. methanol and stained with 0.5% Crystal violet. Colonies were imaged in camera and counted using Image J (FIJI).

6. Cell Images

Cell images were taken in Eclipase TS100 Nikon light microscope in 10×/0.25 Ph1 ADL lens and captured by Digital sight DS-U3 Nikon camera.

For each kit 20,000 cells of either A2780 or U87 cell lines were seeded in inovitro dishes and treated with TTFields. Lysate was prepared after indicated time as described in Luminex protocol. For each well 500 microgram of lysate were loaded.

7. Immunohistochemistry Analysis

Samples were taken from Sprague Dawley rats that were injected orthotopically with N1-S1 hepatocellular carcinoma cells and treated for 6 days with either TTFields at 150 kHz or heat as sham. Tumors were paraffin embedded and stained by immunohistochemistry for phospho-AKT Ser473 (with specific antibody Sigma, Cat #05-1003)) by Patho-Logica. Slides were scanned in an automated slide scanner 3DHistech Panoramic 259 Flash III at the Biomedical Core Facility at the Rapport Faculty of Medicine, Technion. Analysis was performed by Fiji, Image G.

B. Results

The schematic in FIG. 1 is a representation of the cyclin D1 pathway. Cells undergoing DNA damage response activate CDK4-Cyclin D1 to generate mono-phosphorylated Retinoblastoma tumor suppressor protein (Rb). Cells exiting the cell cycle use an un-phosphorylated Rb. CDK4-Cyclin D1 and CDK2-Cyclin E complexes must phosphorylate Rb in order to progress cells into S phase. Rb has been shown to inhibit E2F-induced apoptosis by repressing E2F gene expression. When Rb carboxy terminus is phosphorylated by CDK4-Cyclin D1, E2F1 is released from the complex and upregulates proapoptotic genes.

TTFields reduced levels of cyclin D1 either by degradation or inhibiting its transcription. As a result, there is an increase in mTORC2 activation leading to an increase in Aid survival signaling that reduces treatment efficacy. Inhibiting this pathway in locations I and II, as seen in scheme, by mTOR inhibitors or Akt inhibitors can result in higher efficacy of treatment in combination with TTFields.

FIGS. 2A-2C shows that TTFields application leads to a decrease in cyclin D1 protein levels. Levels of cyclin D1 protein were examined by western blot in lysates produced from (FIG. 2A) H1299 a human non-small cell lung carcinoma cell line, (FIG. 2B) U87 or (FIG. 2C) LN229 human glioblastoma cell lines in untreated cells (left) compared to cells that have undergone TTFields application for 48 or 72 hours as specified in FIGS. 2A-2C. Western blot results are presented and are quantified relative to housekeeping gene expression (vinculin or GAPDH as shown in FIGS. 2A-2C) in graphs presented below images.

Figures 3A, 3B:
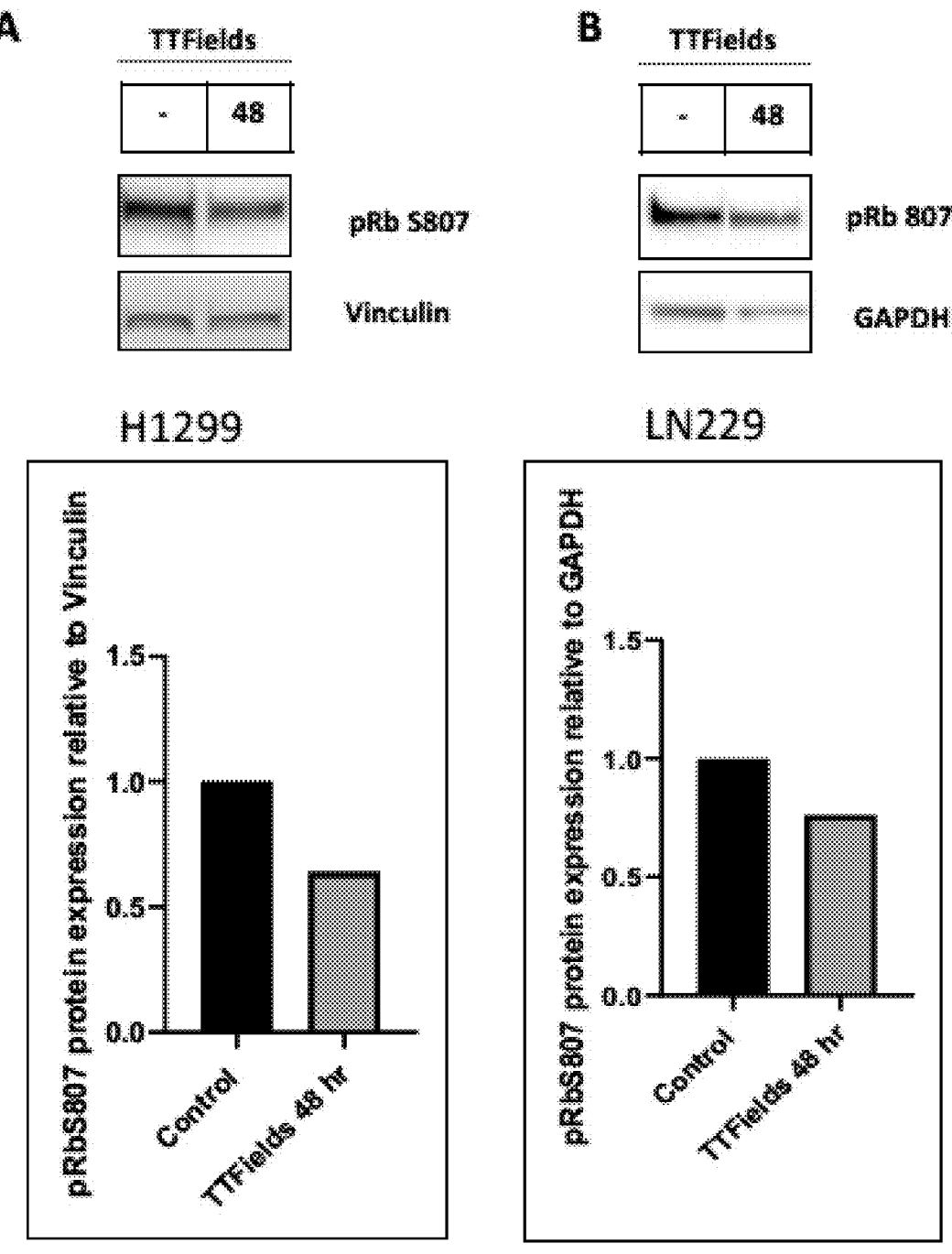
FIG. 3A and FIG. 3B show that TTFields application reduces phosphorylation of Rb in Ser807/811.

FIGS. 3A-3B shows TTFields application reduces phosphorylation of Rb in Ser807/811. Levels of pRb Ser807/811 protein were examined by western blot in lysates produced from (FIG. 3A) H1299 a human non-small cell lung carcinoma cell line, (FIG. 3B) LN229 human glioblastoma cell line in untreated cells (left) compared to cells that have undergone TTFields application for 48 or 72 hours as specified in FIG. 3A and FIG. 3B. Western blot results are presented relative to housekeeping gene expression (vinculin or GAPDH as shown in FIG. 3A and FIG. 3B) and are quantified in graphs presented below images.

Figures 4A, 4B:
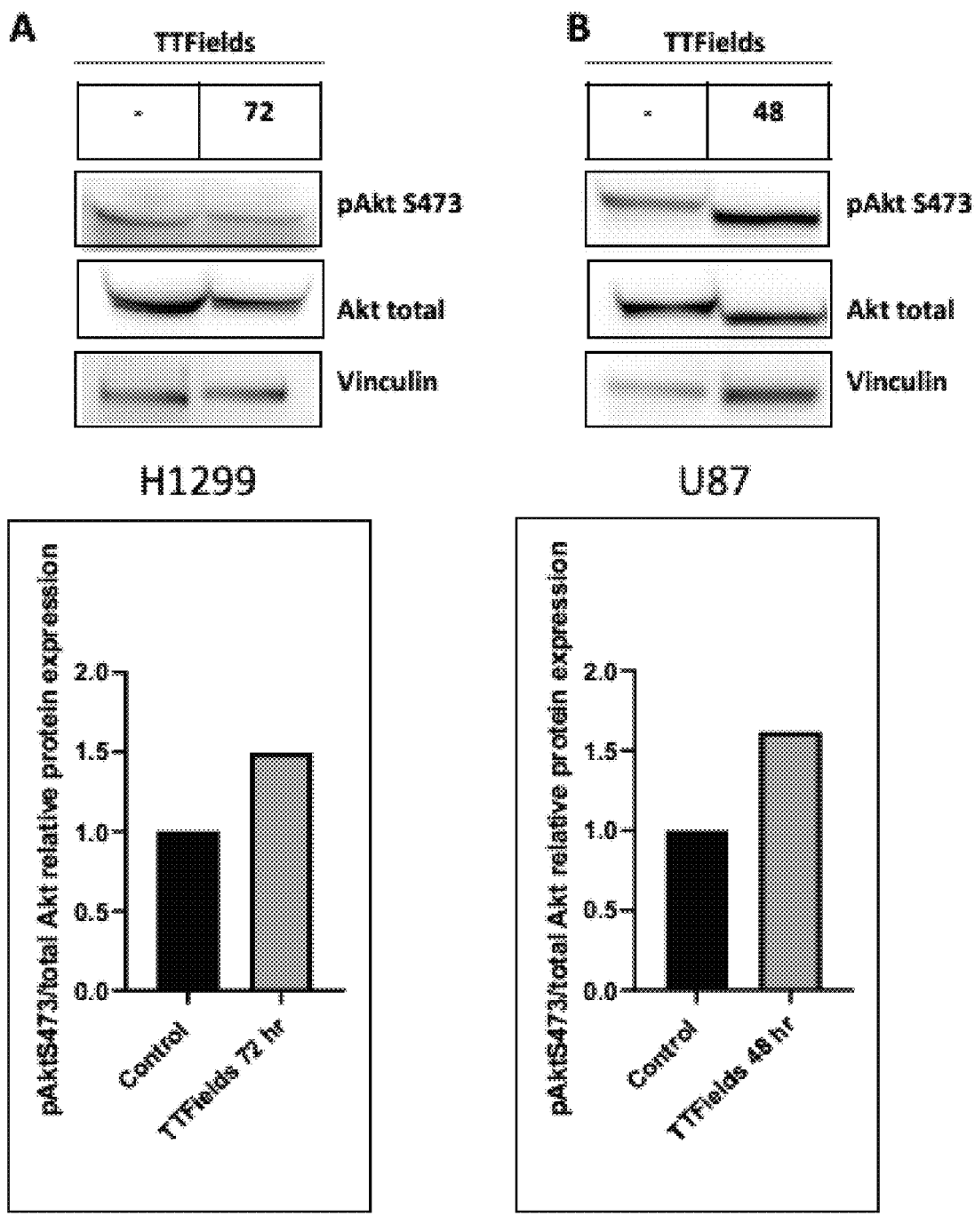
FIG. 4A and FIG. 4B show TTFields application increases phosphorylation of Akt in Ser473.
Figures 5A, 5B:
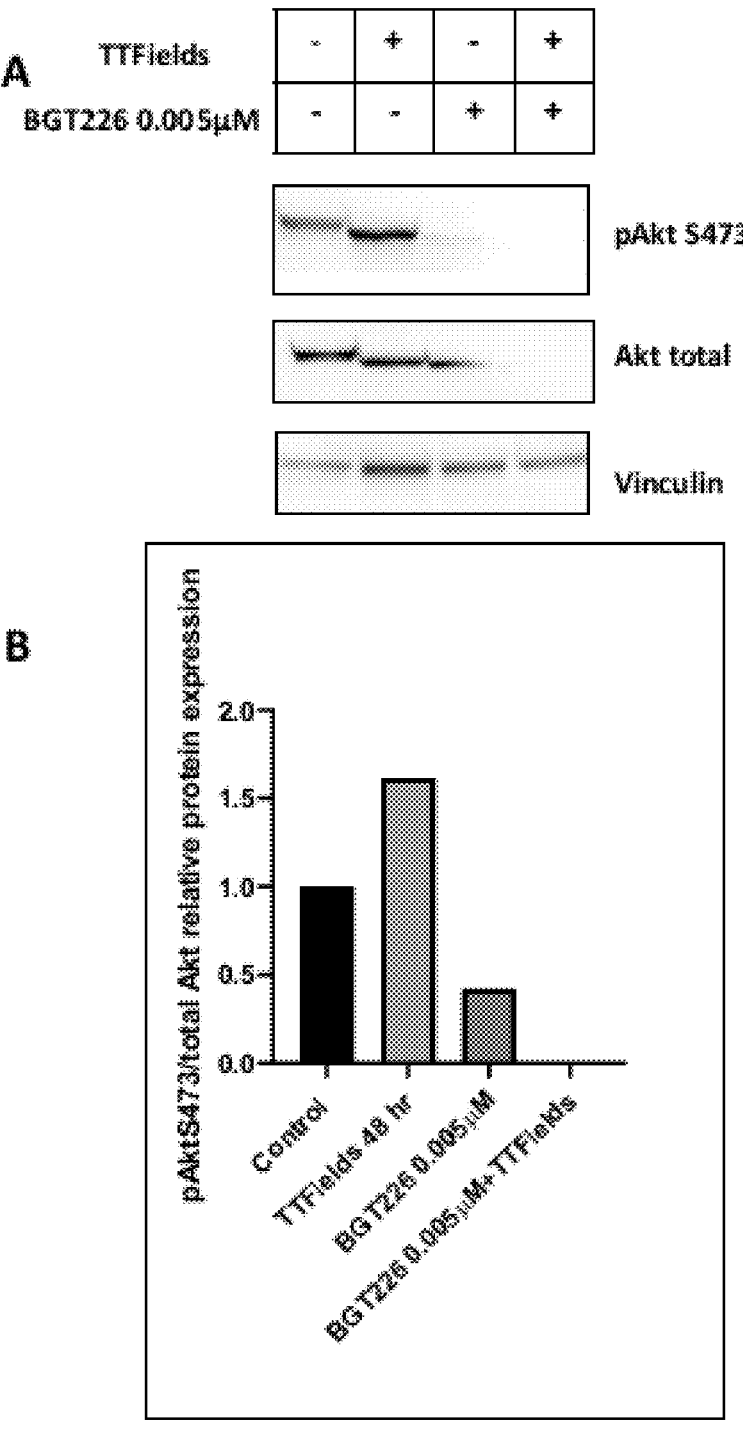
FIG. 5A and FIG. 5B shows a combination of TTFields and mTOR inhibitors results in a synergistic effect.
Figure 6A:
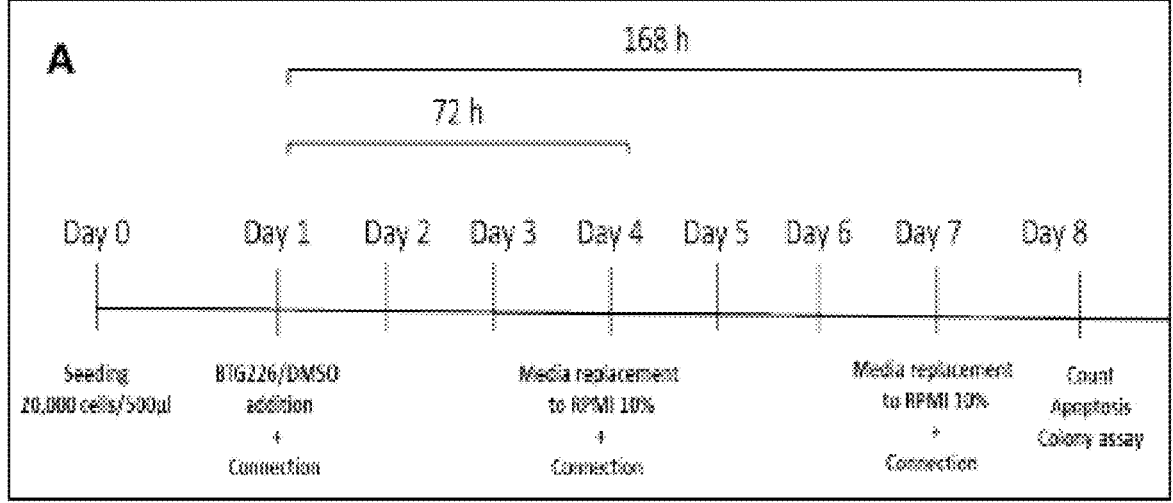
FIGS. 6A-6E show cell resistance caused by pro-survival signaling by TTFields is inhibited by BGT226, a dual PI3K/mTOR inhibitor.
Figure 6B:
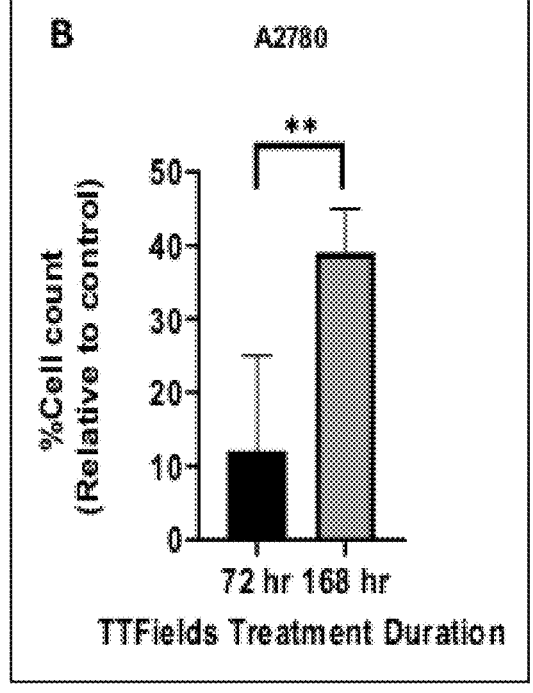
Figure 6C:
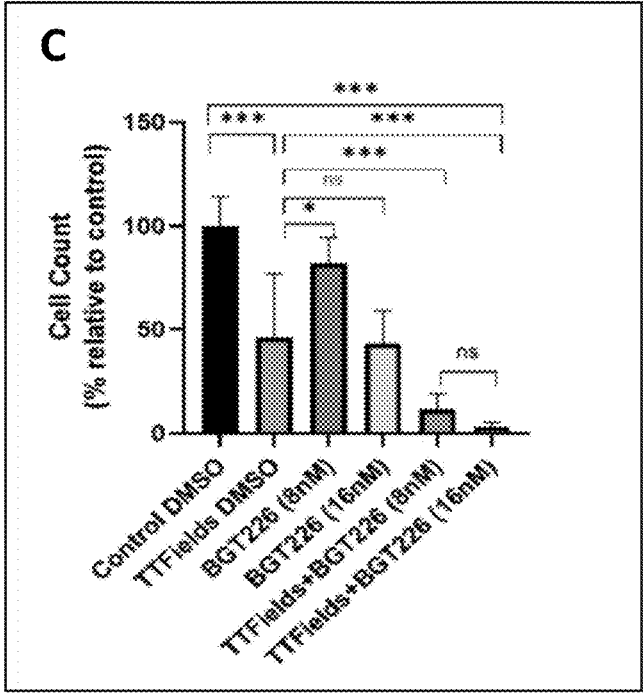
Figures 6D, 6E:
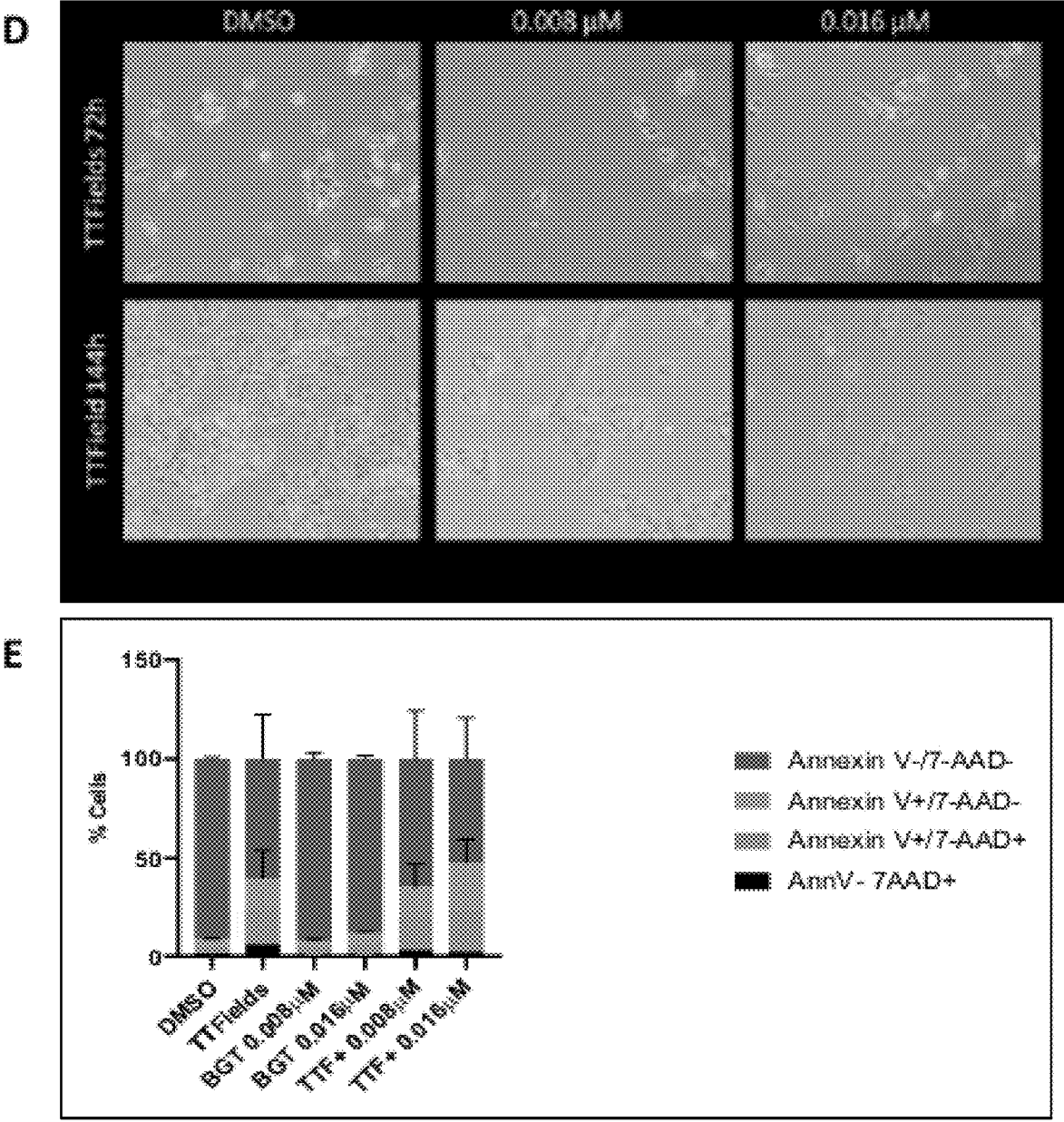

FIGS. 4A-4B shows TTFields application increases phosphorylation of Akt in Ser473. Levels of pAkt ser473 protein and Akt total protein were examined by western blot in lysates produced from (FIG. 4A) H1299 a human non-small cell lung carcinoma cell line, (FIG. 4B) U87 human glioblastoma cell line in untreated cells compared to cells that have undergone TTFields application for 48 or 72 hours as specified in FIG. 4 and FIG. 4B. Western blot results are presented relative to housekeeping gene expression (vinculin or GAPDH as shown in FIG. 4 and FIG. 4B) and are quantified in graphs presented in FIG. 4 and FIG. 4B. However, a decrease in phosphorylation of Akt in Ser473 was observed following combined treatment of TTFields and BGT226. BGT226 was added to cells 12-24 hours after seeding for inhibitor mono-treatment and combination treatment to a final concentration of 5 nM in A2780 cells and control and TTFields samples received same volume of DMSO. Following 72 hours of treatment media was replaced for media with no inhibitor and cells were grown for additional 96 hours. At 168 hours (7 days) cell lysate was produced and run on SDS-PAGE as described in method section FIGS. 5A-5B shows the combination of TTFields and mTOR inhibitors results in a synergistic effect. Western blot analysis showed an increase in Akt phosphorylation following TTFields that was inhibited by BGT226, a PI3K/mTOR inhibitor. (FIG. 5A) Western blot results are presented relative to housekeeping gene expression (vinculin or GAPDH as shown in FIG. 5A and FIG. 5B) and are quantified in graphs presented below images (FIG. 5B).

FIGS. 6A-6E shows cell resistance caused by pro-survival signaling by TTFields is inhibited by BGT226, a dual PI3K/mTOR inhibitor. (FIG. 6A) schematic representation of treatment. (FIG. 6B) Cells that undergo TTFields treatment exhibit a resistance in longer duration of treatment. Cells were counted following 72 hours (black) and 168 hours (gray) of treatment and showed that following 168 hours there are more cells compared to 72 hours indicating a pro-survival mechanism. (FIG. 6C) Combination of TTFields with BGT226 resulted in a synergistic effect in cell survival. (FIG. 6D) Images of cells after 72 hours (upper panel) or 144 hours (lower panel) TTFields in mono-treatment or combined with BGT226. Cells that had received combined treatment do not recover (seen by confluency of cells in the area presented) opposed to cells following 144 hours of TTFields treatment alone. (FIG. 6E) Results of apoptotic assay show that combined treatment of TTFields induce apoptosis in reminder of cells. Cells that were treated with inhibitor alone showed more live cells (AnnexinV-/7AAD-cells in dark gray) compared to cells that were treated with combined treatment. Statistical analysis was performed by one-way ANOVA statistical test*pValue<0.05, pValue<0.01, *pValue<0.001 in regards to indicated columns in graph.

Figure 7:
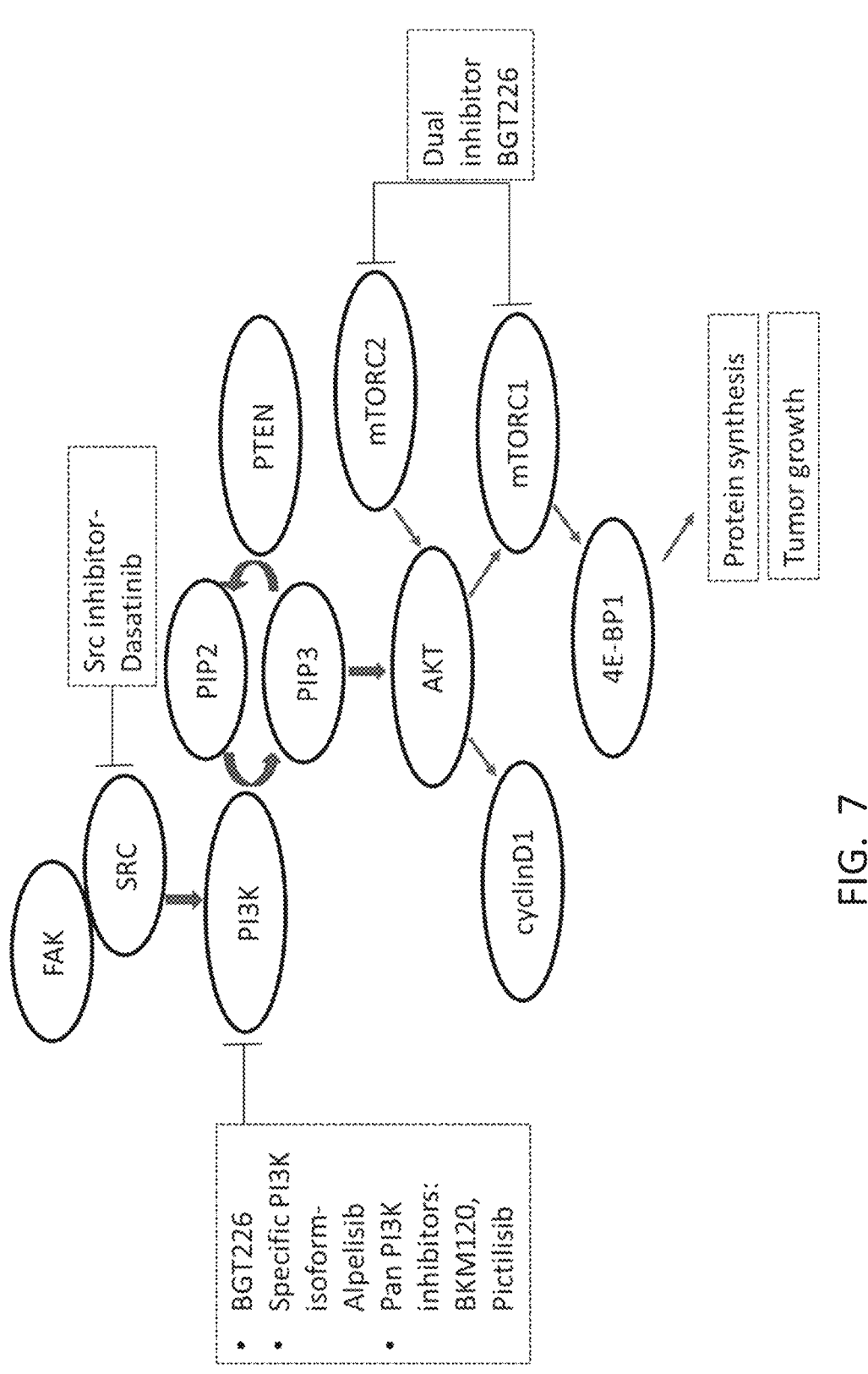
FIG. 7 shows a schematic diagram showing the influence of PI3K pan inhibitors on Akt phosphorylation and subsequently on mTORC2 complex activation.

FIG. 7 shows a schematic diagram showing the influence of PI3K pan inhibitors on Akt phosphorylation and subsequently on mTORC2 complex activation.

Figures 8A, 8B:
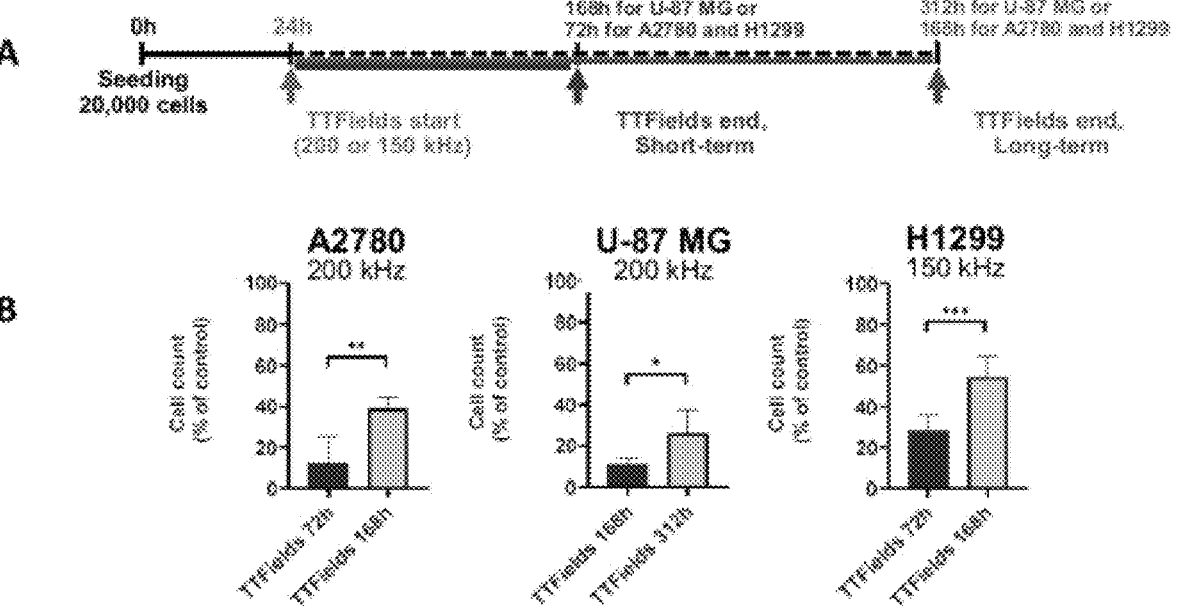
FIG. 8A and FIG. 8B show in vitro-resistant cell lines.

FIGS. 8A and 8B show in vitro-resistant cell lines model; establishment. (FIG. 8A) TTFields were delivered for short term (72 h; represented by red arrows) and long term (168 h/312 h; represented by green arrows) to U-87-MG (200 kHz), H1299 (150 kHz) or A2780 (200 kHz) cells. (FIG. 8B) Cells were examined for cytotoxic effect. Decreased cytotoxicity was observed in all cell lines following long term application of TTFields relative to short term application. Mean+SEM; paired t-test.

Figures 9A, 9B, 9C, 9D:
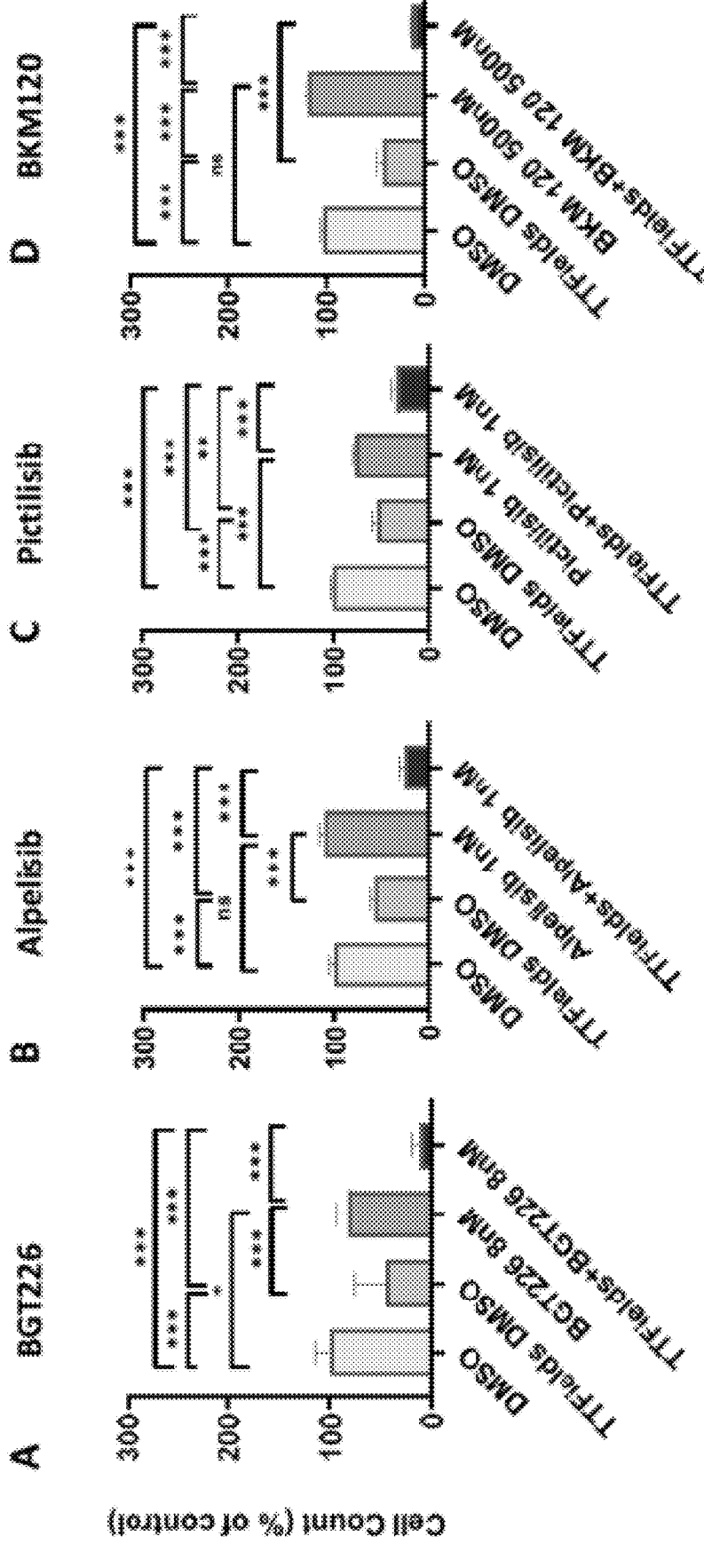
FIGS. 9A-9D show a summary of combination effect of PI3K inhibitors on cytotoxicity.

FIGS. 9-11 show the results of combination treatments of TTFields with different pharmacological inhibitors including a PI3K/mTOR dual inhibitor (BGT226), and Pan- and isoform-specific inhibitors of PI3K (Alpelisib, Pictilisib, and BKM120), at inhibition concentration 25 (IC25) for 72 h. At 72 h, the media was replaced and TTFields were delivered alone for additional 96 h.

FIG. 9 shows cytotoxicity by percentage of cell count compared to control following various treatments. FIG. 10 shows results of apoptosis assay. Of counted cells in the combined treatment a larger percentage of cells are in stages of apoptosis indicating efficacy of treatment. FIG. 11 shows clonogenicity of cells following treatment indicating that surviving cells are less colonogenic following combined treatment. In summary, each of the four inhibitors shown in the figures provided an added effect to the TTFields alone.

FIGS. 9A-9D show a summary of combination effect of PI3K inhibitors on cytotoxicity. In A2780 cell line (FIG. 9A) BGT226, (FIG. 9B) Alpelisib, (FIG. 9C) Pictilisib and (FIG. 9D) BKM120. A2780 cells were treated with TTFields (200 kHz) in combination with specific inhibitor at inhibition concentration 25 (IC25) for 72 h. At 72 h, the media was replaced and TTFields were delivered alone for additional 96 h. (Mean+SEM; *Pvalue<0.05, Pvalue<0.01, *Pvalue<0.005 In a one-way ANOVA, followed by Tukey's post-test).

Figures 10A, 10B, 10C, 10D:
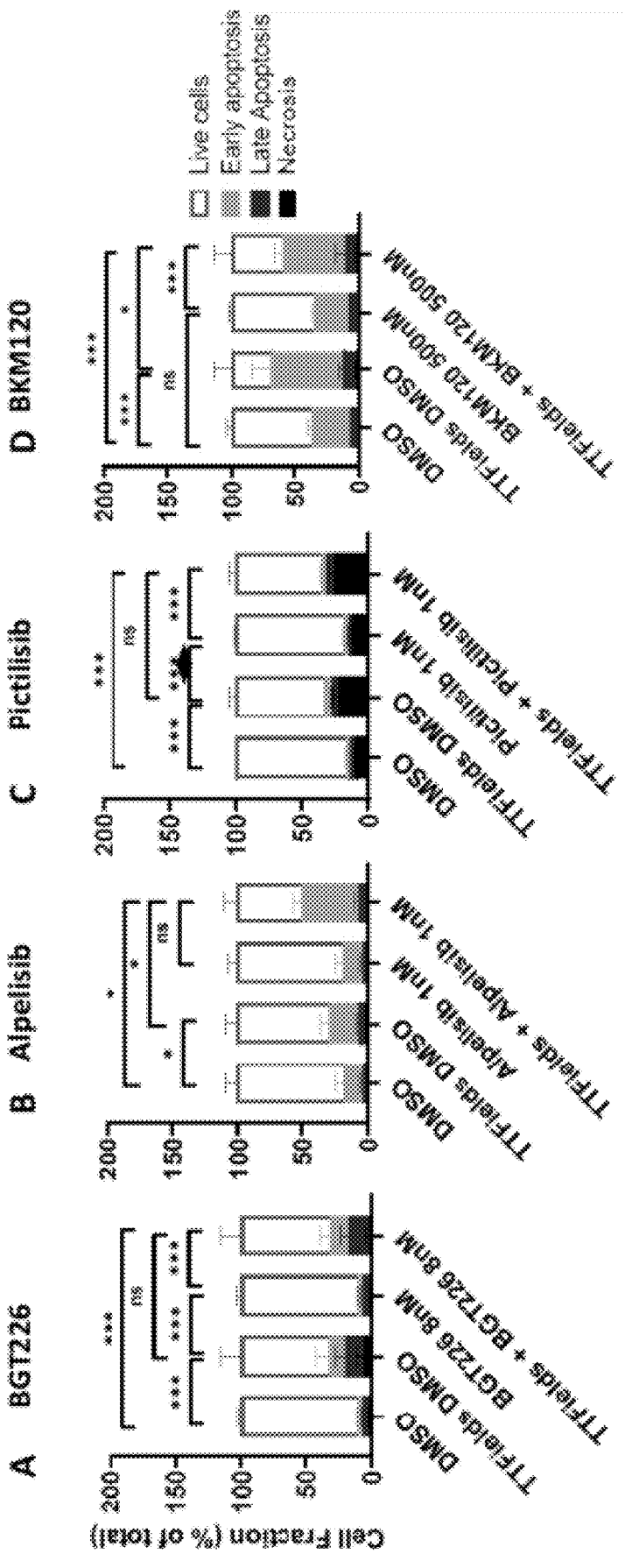
FIGS. 10A-D shows a summary of combination effect of PI3K inhibitors on apoptosis.

FIG. 10 shows a summary of combination effect of PI3K inhibitors on apoptosis. In A2780 cell line (FIG. 10A) BGT226, (FIG. 10B) Alpelisib, (FIG. 10C) Pictilisib and (FIG. 10D) BKM120. A2780 cells were treated with TTFields (200 kHz) in combination with specific inhibitor at inhibition concentration 25 (IC25) for 72 h. At 72 h, the media was replaced and TTFields were delivered alone for additional 96 h. (Mean+SEM; *Pvalue<0.05, Pvalue<0.01, *Pvalue<0.005. In a one-way ANOVA, followed by Tukey's post-test).

Figures 11A, 11B, 11C, 11D:
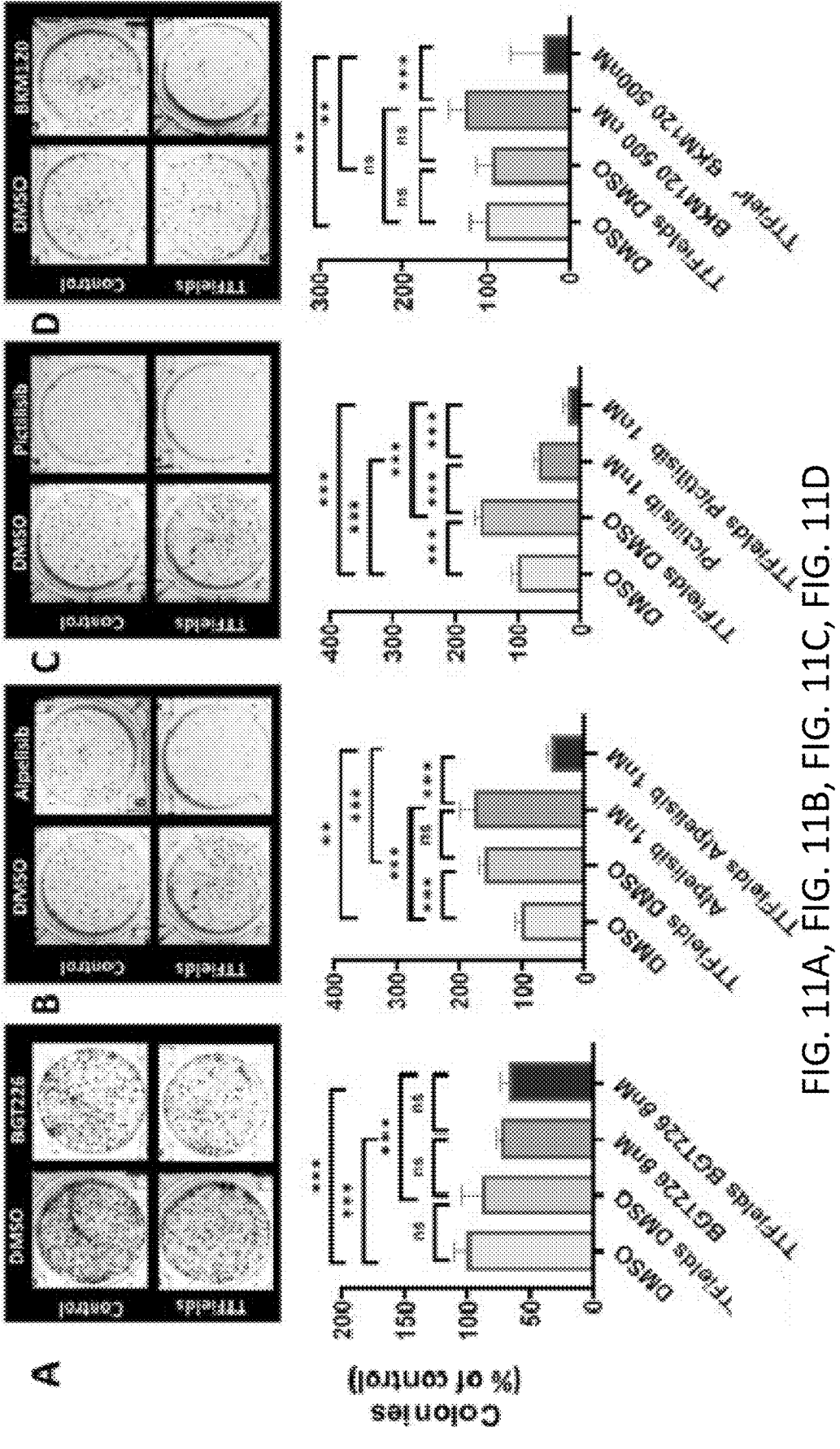
FIG. 11A-11D show a summary of combination effects of PI3K inhibitors on clonogenicity.

FIG. 11 shows a summary of combination effect of PI3K inhibitors on clonogenicity. In A2780 cell line (FIG. 11A) BGT226, (FIG. 11B) Alpelisib, (FIG. 11C) Pictilisib and (FIG. 11D) BKM120. A2780 cells were treated with TTFields (200 kHz) in combination with specific inhibitor at inhibition concentration 25 (IC25) for 72 h. At 72 h, the media was replaced and TTFields were delivered alone for additional 96 h. Upper panel: representative images of colony assay. Bottom panel: graphic representation of quantification of colony assay. (Mean+SEM; *Pvalue<0.05, Pvalue<0.01, *Pvalue<0.005. In a one-way ANOVA, followed by Tukey's post-test).).

Figure 12:
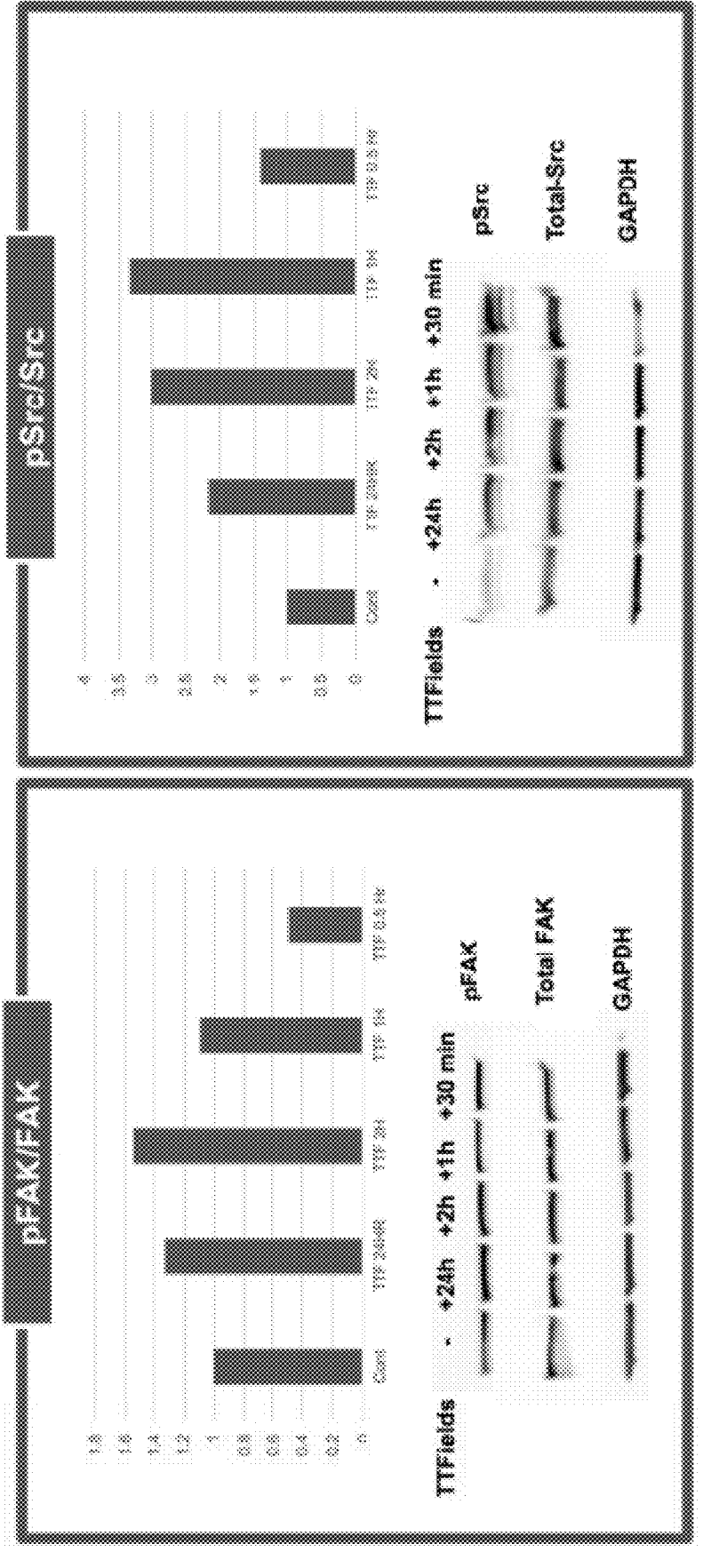
FIG. 12 shows molecular signaling of TTFields in A2780. Western blot analysis of protein lysates following short times of TTFields application showed an increase in activation of the Src/FAK pathway.

FIG. 12 shows molecular signaling of TTFields in A2780. western blot analysis of protein lysates following short times of TTFields application showed an increase in activation of the Src/FAK pathway. Upper panel-Graphical representation of quantification of western blot bands presented in lower panel showing protein expression of either phospho-FAK (Tyr 397) (left) or phospho-Src (Tyr416) (right) compared to total protein of FAK (left) or Src (right) relative to GADPH, housekeeping protein expression.

Figure 13:
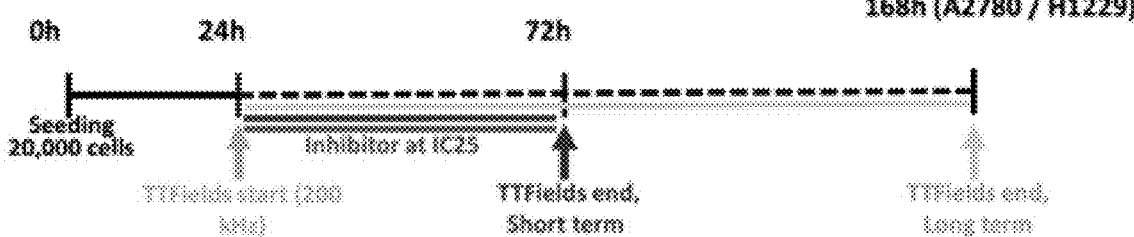
FIG. 13 shows the combination of TTFields with Src inhibitor.

FIG. 13 shows the combination of TTFields with Src inhibitor, Dasatinib showed increased treatment efficacy relative to TTFields or inhibitor alone in all combination groups. A2780 and H1299 cells were treated with TTFields (200 kHz for A2780 and 150 kHz for H1299) in combination with Dasatinib, a Src inhibitor. at inhibition concentration 25 (IC25) for 72 h (represented by red line). At 72 h, the media was replaced and TTFields were delivered alone for additional 96 h (represented by black dashed line).

Figure 14:
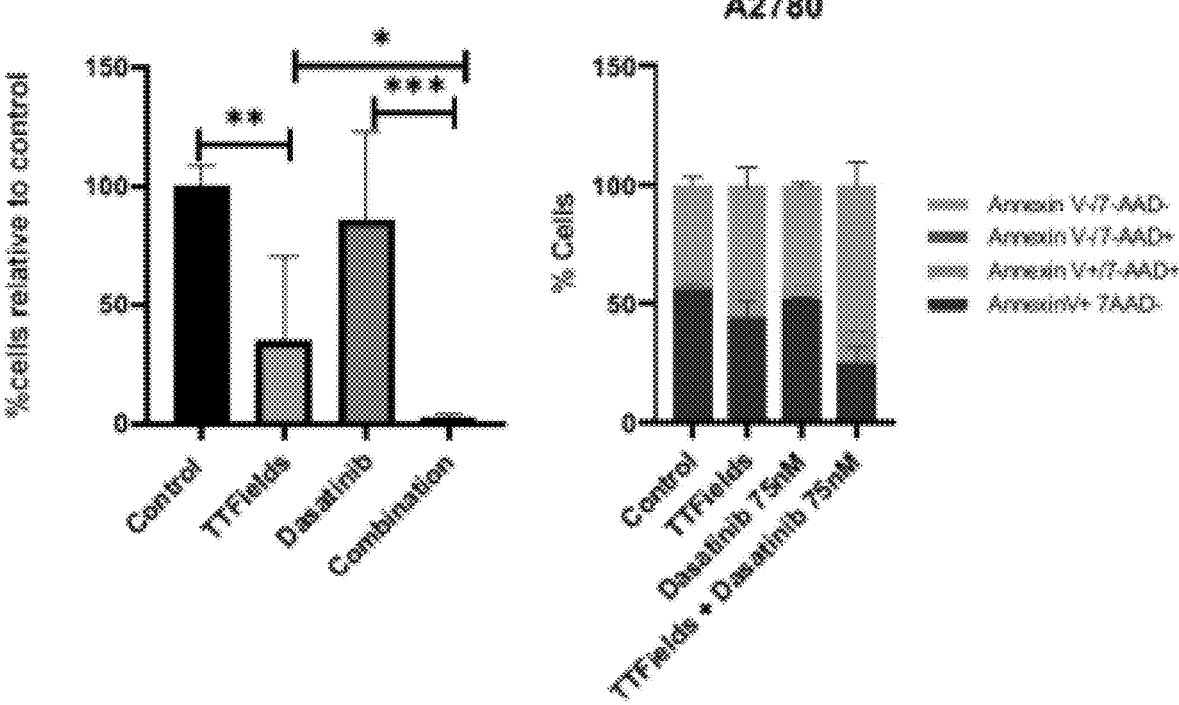
FIG. 14 shows the combination of TTFields with Src inhibitor, Dasatinib showed increased treatment efficacy relative to TTFields or inhibitor alone.

FIG. 14 shows the combination of TTFields with Src inhibitor, Dasatinib showed increased treatment efficacy relative to TTFields or inhibitor alone. Left-cytotoxic effect of treatment on A2780 cells, Right-Apoptotic effect following either monotreatment with TTFields or 0.075 μM Dasatinib compared with combination treatment. (Mean+SEM; one-way ANOVA, followed by Tukey's post-test). *Pvalue<0.05, Pvalue<0.01, *Pvalue<0.005.

FIG. 15 shows the combination of TTFields with Src inhibitor on clonogenicity. Results of colonogenic effect on A2780 cell line following combination treatment with TTFields and Dasatinib. Left-representative images, right-quantification of results. (Mean+SEM; one-way ANOVA, followed by Tukey's post-test). *Pvalue<0.05 or ***Pvalue<0.005

Figure 16:
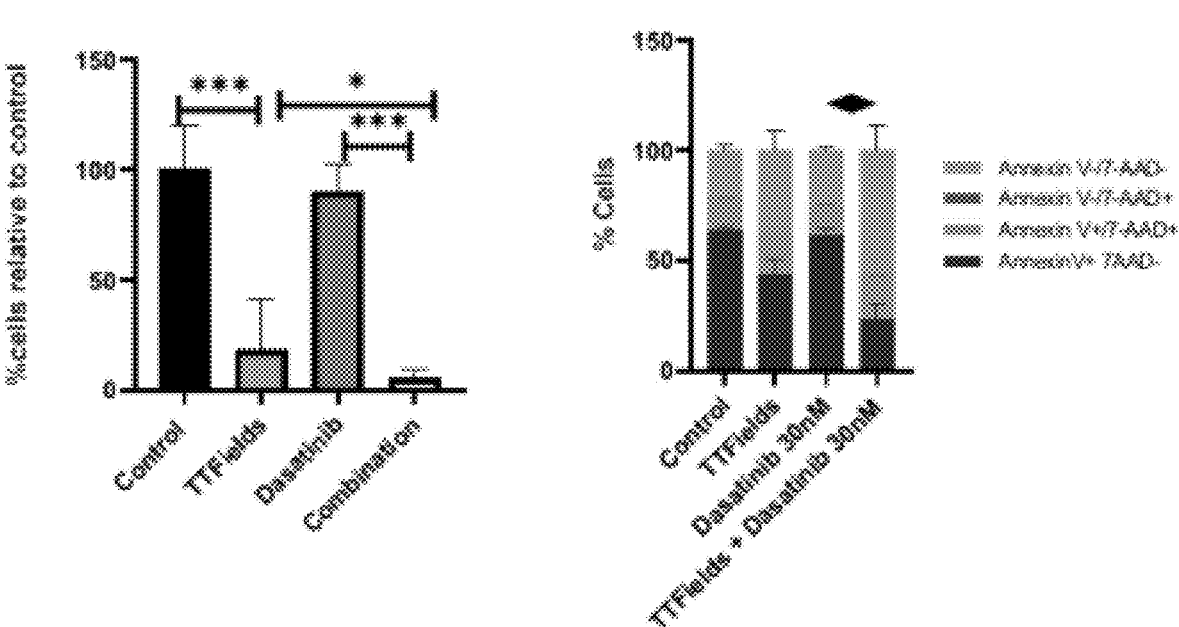
FIG. 16 shows the combination of TTFields with Src inhibitor, Dasatinib.

FIG. 16 shows the combination of TTFields with Src inhibitor, Dasatinib showed increased treatment efficacy relative to TTFields or inhibitor alone. Left-cytotoxic effect of treatment on H1299 cells, Right-Apoptotic effect following either monotreatment with TTFields or 0.03 μM Dasatinib compared with combination treatment. (Mean+SEM; one-way ANOVA, followed by Tukey's post-test). *Pvalue<0.05 or ***Pvalue<0.005.

Figure 17:
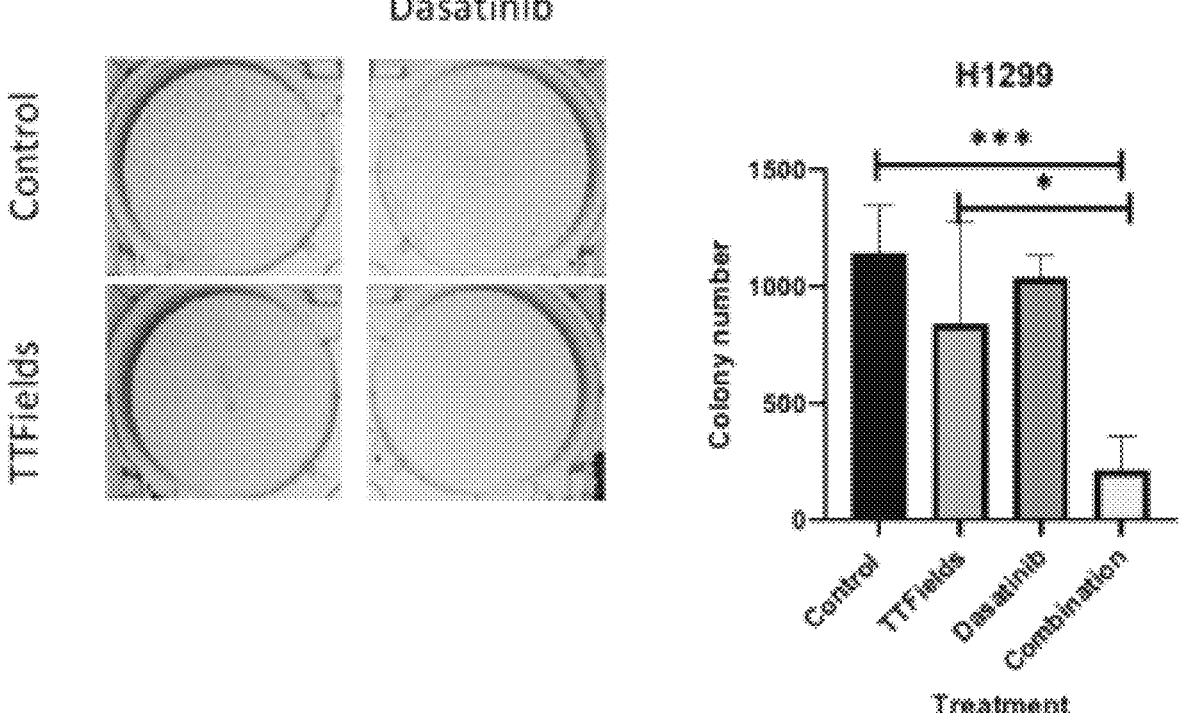
FIG. 17 shows the combination of TTFields with Src inhibitor on colonogenicity.
Figure 18:
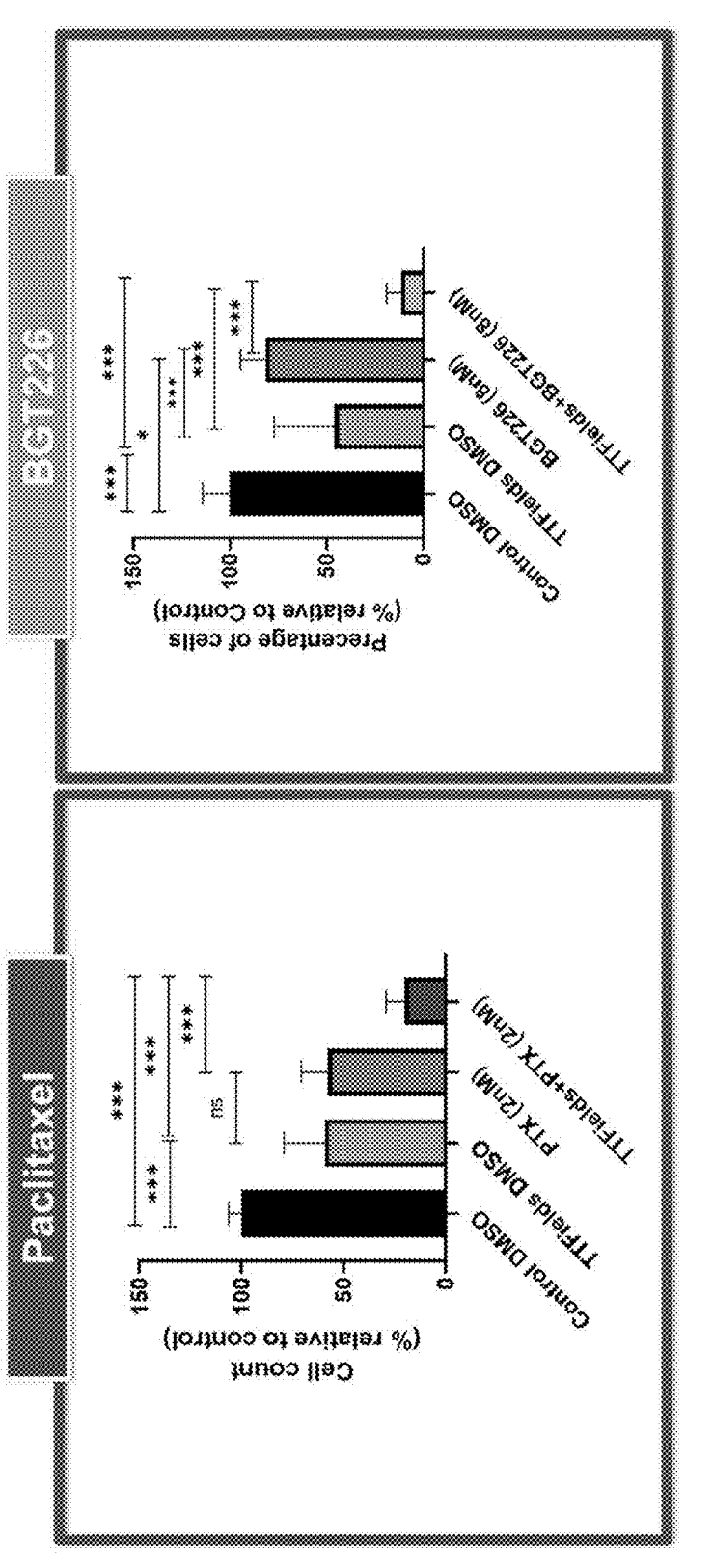
FIG. 18 shows the combination therapy of BGT226 with TTFields is more effective than Paclitaxel and TTFields.
Figure 19:
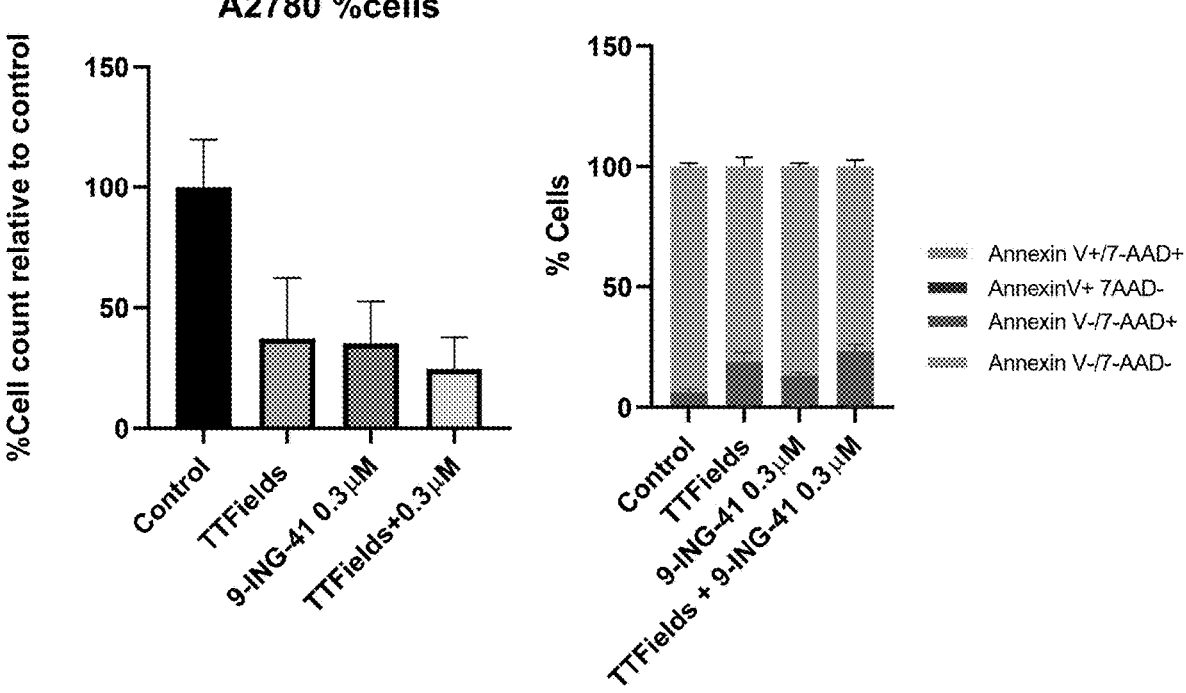
FIG. 19 shows the combination therapy of GSK3β inhibitor with TTFields is not more effective than TTFields alone

FIG. 17 shows the combination of TTFields with Src inhibitor on colonogenicity. Results of colonogenic effect on H1299 cell line following combination treatment with TTFields and Dasatinib. Left-representative images, right-quantification of results. (Mean+SEM; one-way ANOVA, followed by Tukey's post-test). *Pvalue<0.05 or *Pvalue<0.005 FIG. 18 shows the comparison of treating with a combination of BGT226 with TTFields is more effective than Paclitaxel and TTFields. Cells in both treatments (BGT226 8 nM or Paclitaxel 2 nM) were seeded in inovitro dishes and 12-24 hours after seeding either BGT226 at 8 nm or Paclitaxel at 2 nM were added at inhibition concentration 25 (IC25) for 72 h. At 72 h, the media was replaced and TTFields were delivered alone for additional 96 h. While results of cytotoxicity show that combination with paclitaxel is effective to a lesser extent than that of BGT226 in clonogenicity there is a dramatic effect in combination therapy with BGT226 compared to Paclitaxel FIG. 19** shows that combination therapy with GSK3β inhibitor 9-ING-41 did not increase efficacy of TTFields treatment in cell cytotoxicity or apoptosis.

C. GSK Experiments

The combination of TTFields and GSK3beta inhibitors can be used. For example, below is a treatment plan for GSK3beta inhibitor 9-ING-41.

Treatment groups can be: 1) Control group; 2) TTFields mono-treatment; 3) 9-ING-41 monotreatment 0.1-5 μM (based on titration that will be performed); and 4) a combination therapy of TTFields and 9-ING-41.

The duration of treatment can be examined in U87 human glioblastoma and A2780 human ovarian carcinoma cell lines (based on pervious work done with mTOR inhibitor BGT226) and the duration of treatment can be between 24 hours to 72 hours.

Treatment efficacy and cell resistance can be examined by cell count, apoptosis assay and colony assay for 24 to 168 hours (to be decided at a later time point based on preliminary experiments and titration of the inhibitor 9-ING-41).

Those skilled in the art will recognize, or be able to ascertain using no more than routine experimentation, many equivalents to the specific embodiments of the method and compositions described herein. Such equivalents are intended to be encompassed by the following claims.

We claim:

1. A method of increasing sensitivity of a cancer cell to alternating electric fields comprising:
    (a) exposing the cancer cell to low intensity alternating electric fields for a period of time, wherein the low intensity alternating electric fields have a field strength between 0.1-10 V/cm, and
    (b) exposing the cancer cell to an mTOR inhibitor, AKT inhibitor, PI3K inhibitor, Src inhibitor, or FAK inhibitor.

2. The method of claim 1, wherein the low intensity alternating electric fields have a frequency between 100 and 500 kHz.

3. The method of claim 1, wherein the cancer cell is a glioblastoma cell, ovarian cancer cell, or metastatic lung carcinoma cell.

4. The method of claim 1, wherein the cancer cell is in a subject.

5. The method of claim 1, wherein the cancer cell is exposed to the low intensity alternating electric fields and the mTOR inhibitor, AKT inhibitor, PI3K inhibitor, Src inhibitor, or FAK inhibitor simultaneously.

6. The method of claim 1, wherein the mTOR inhibitor is selected from one or more of the group consisting of: torkinibs, everolimus, temsirolimus (CCI-779), Rapamycin (Sirolimus), everolimus, CC-223, MKK-1, AZD8055, AZD02114, INK-128, CC-223, 051-027, dactolisib, BGT226, SF1126, PKI-587, NVPBE235, sapanisertib, AZD8055, AZD2014, BEZ235, XL765, GDC0980, SF1126, PF-04691502, PF-052123384 (gedatosilib), LY3023414, PF-05212384 (Gedatolisib, PKI-587), XL795 (voxtasilib), Bimiralisib (PQR309), Paxalisib (GDC-0084), DS-7423, PKI-179, GSK458V, P7170, SB2343, Rapalink-1, PI-103, NU7441, KU-0063794, Ridaforolimus (deforolimus, MK-8669), Torin 1, Torin 2, OSI-027, GSK1059615, WYE-354, Vistusertib (AZD2014), WYE-125132, Palomid 529 (P529), WYE-687, XL388, MHY1485, LY3023414 (Samotolisib), GNE-447, CC-115, Zotarolimus (ABT-578), PQR620, SF2523, mTor inhibitor-1,2,3 or 8, PRQ626, WAY-600, .PF-04979064, 3BDO, Dihydromyricetin, ETP-46464, PKI-402, Cyclovirbuxine D, CZ415, VS-5584, (+)-usunic acid, RMC-5552, PRQ530, JR-AB2-011, Arnicolide D or TML-6.

7. The method of claim 1, wherein the AKT inhibitor is lapatinib, H 8, H 89, NL 71 101, GSK690693, 7 azaindole, 6 phenylpurine derivatives, pyrrolo[2,3 d]pyrimidine derivatives, CCT128930, 3 aminopyrrolidine, anilinotriazole derivatives, spiroindoline derivatives, AZD5363, ipatasertib (GDC 0068, RG7440), A 674563, A 443654, AT7867, AT13148, Afuresertib (GSK2110183), 2 pyrimidyl 5 amidothiophene derivative (DC120), uprosertib (GSK2141795), 2,3 diphenylquinoxaline derivatives, triazolo[3,4 f][1,6]naphthyridin 3(2H) one derivative (MK 2206) Edelfosine (1 O octadecyl 2 O methyl rac glycero 3 phosphocholine, ET-18-OCH3) ilmofosine (BM 41.440), miltefosine (hexadecylphosphocholine, HePC), perifosine (D 21266), erucylphosphocholine (ErPC), erufosine (ErPC3, erucylphosphohomocholine), Indole 3 carbinol, 3 chloroacetylindole, diindolylmethane, diethyl 6 methoxy 5,7 dihydroindolo [2,3 b]carbazole 2,10 dicarboxylate (SR13668), OSU A9, PH 316, PHT 427, PIT 1, PIT 2, M PIT 1, [(1 methyl 1H pyrazol 4 yl)carbonyl] N' (3 bromophenyl) thiourea, Triciribine (TCN, NSC 154020), triciribine mono phosphate active analogue (TCN P), 4 amino pyrido[2,3 d]pyrimidine derivative API 1, 3 phenyl 3H imidazo[4,5 b]pyridine derivatives, ARQ 092, BAY 1125976, 3 methyl xanthine, quinoline 4 carboxamide and 2 [4 (cyclohexa 1,3 dien 1 yl) 1H pyrazol 3 yl]phenol, 3 oxo tirucallic acid, 3α- and 3β acetoxy tirucallic acids, acetoxy tirucallic, Lactoquinomycin, Frenolicin B, kalafungin, medermycin, Boc Phe vinyl ketone, 4 hydroxynonenal (4 HNE), 1,6 naphthyridinone derivatives, imidazol 1,2 pyridine derivatives, Rigosertib (ON-01910), Triciribine, Honokiol, Miransertib (ARQ 092), Borussertib, SC66), A-674563, TIC10 analogue, Urolithin B, ABTL-0821, Loureirin A, Homosalate, Deguelin, Resibfogenin, Terameprocol, Oroxin B, LM22B-10, Amarogentin, Oridonin, Praeruptorin A, or Scutellarin.

8. The method of claim 1, wherein the PI3K inhibitor is one of: BKM120, XL147, PX-866, GCD-0941, GDC-0032, BAY 80-6946, ZSTK474, AMG 511, BYL719, MLN1117, CAL-101, GSK2636771, CH5132799, AMG319, AZD6482, TG100-115, AZD8835, WX-037, AZD8186, KA2237, CAL-120, ME401, INCB050465, INK-1117, TGR-1202, RP6530, IPI-145, 3-Hydroxyanthranilic acid, Hispidulin, Pectolinarin, and Cinobufagin.

9. The method of claim 1, wherein the Src inhibitor is Dasatinib (BMS-354825), Ponatinib (AP24534), Saracatinib (AZD0530), Bosutinib (SKI-606), Dehydroabietic acid (DAA, DHAA), PP2, Ginkgolic acid C17:1 (GAC 17:1), DGY-06-116, Doramapimod (BIRB 796), Apatinib, Pelitinib (EKB-569), Resveratrol, KX2-391 (Tirabanibulin), NVP-BHG712, ENMD-2076, PRT062607 (P505-15, BIIB057, PRT-2607), PP1, MNS(3,4 Methylenedioxy-β-nitrostyrene), Doramapimod (BIRB 796), WH-4-023, RK24466, KX1-004, 7-Hydroxychromone, AD-80, Repotrectinib (TPX-0005), Quercetin (NSC 9221, Sophoretin, C.I. 75720), SU 6656, Src Inhibitor 1 (CAS 179248-59-0), CCT196969, Myristic acid (Tetradecanoic acid), eCF506, 1-Naphthyl PP1(1-NA-PP 1), AMG-47a, ON123300, UM-164, MLR-1023.PD173955, AZD0424, PD180970 or HG-7-85-01.

10. The method of claim 1, further comprising increasing cyclin D1 protein levels in the cancer cell.

11. The method of claim 10, wherein the cancer cells are exposed to the low intensity alternating electric fields and cyclin D1 protein levels are restored to levels prior to exposing to the low intensity alternating electric fields simultaneously.

12. The method of claim 10, wherein the cancer cells are exposed to the low intensity alternating electric fields, and the mTOR inhibitor, AKT inhibitor, PI3K inhibitor, Src inhibitor or FAK inhibitor simultaneously and cyclin D1 protein levels are restored to levels prior to exposing to the low intensity alternating electric fields simultaneously.

13. The method of claim 1, wherein the Fak inhibitor is Defectanib (VS-6063), Solanesol (nonaisoprenol), PF-00562271 Besylate (PF-562271), PF-562271 (PF-00562271), PRT062607 (P505-15, BIIB057, PRT-2607), PF-573228 TAE226 (NVP-TAE226), PF-562271 HCl, BI-4464, Y15, GSK2256098, PND-1186(VS-4718), PF-431396, FAK inhibitor 14 (cas 4506-66-5) or Rebastinib.

14. A method of treating a subject having cancer comprising
    (a) applying low intensity alternating electric fields to a target site of the subject for a period of time, wherein the low intensity alternating electric fields have a field strength between 0.1-10 V/cm,
    wherein the target site comprises one or more cancer cells, and (b) administering a therapeutically effective amount of an mTOR inhibitor, AKT inhibitor, PI3K inhibitor, Src inhibitor or FAK inhibitor to the subject.

15. The method of claim 14, wherein the mTOR inhibitor, AKT inhibitor, PI3K inhibitor, Src inhibitor or FAK inhibitor is administered prior to, after, or simultaneously with applying the low intensity alternating electric fields.

16. The method of claim 14, wherein the cancer is glioblastoma, ovarian cancer, or metastatic lung carcinoma.

17. A method of reducing viability of a cancer cell in a subject comprising (a) applying low intensity alternating electric fields to a target site of the subject for a period of time wherein the low intensity alternating electric fields have a field strength between 0.1-10 V/cm, wherein the target site comprises one or more cancer cells, and (b) administering a therapeutically effective amount of an mTOR inhibitor, AKT inhibitor, PI3K inhibitor, Src inhibitor or FAK inhibitor to the subject.

18. The method of claim 17, wherein the cancer is glioblastoma, ovarian cancer, or metastatic lung carcinoma.

\* \* \* \* \*